United States Patent [19]

Walker et al.

[11] Patent Number: 4,792,561

[45] Date of Patent: Dec. 20, 1988

[54] CARBOSTYRIL DERIVATIVES AS COMBINED THROMBOXANE SYNTHETASE AND CYCLIC-AMP PHOSPHODIESTERASE INHIBITORS

[75] Inventors: Keith A. M. Walker, Los Altos Hills; John J. Bruno, Redwood City; Gregory R. Martinez, Palo Alto, all of Calif.

[73] Assignee: Syntex (U.S.A.) Inc., Palo Alto, Calif.

[21] Appl. No.: 868,845

[22] Filed: May 29, 1986

[51] Int. Cl.4 ............... C07D 401/06; C07D 401/10; C07D 401/12; A61K 31/47

[52] U.S. Cl. .................................. 514/312; 546/157; 546/158; 546/13; 548/335; 548/337

[58] Field of Search ............... 514/312; 546/157, 158

[56] References Cited

U.S. PATENT DOCUMENTS

| | | | |
|---|---|---|---|
| 3,962,445 | 6/1976 | Buckle et al. | 514/312 |
| 4,309,432 | 1/1982 | Tanaka et al. | 514/312 |
| 4,359,475 | 11/1982 | Walker | 548/336 |
| 4,442,106 | 4/1984 | Trijzelaar et al. | 546/157 |
| 4,455,422 | 6/1984 | Banno et al. | 546/158 |
| 4,482,560 | 11/1984 | Banno et al. | 546/157 |
| 4,487,772 | 12/1984 | Tominaga et al. | 514/312 |
| 4,530,930 | 7/1985 | Uno et al. | 514/312 |
| 4,608,388 | 8/1986 | Kluge et al. | 514/510 |
| 4,728,653 | 3/1988 | Campbell et al. | 546/157 |

FOREIGN PATENT DOCUMENTS

| | | | |
|---|---|---|---|
| 148623 | 3/1985 | European Pat. Off. | |
| 166533 | 1/1986 | European Pat. Off. | 546/157 |
| 12384 | 1/1979 | Japan . | |
| 83749 | 6/1980 | Japan | 546/157 |

OTHER PUBLICATIONS

Chemical Abstract of Japan for Japan Patent 12384 (1/30/79).
Derwent Abstract No. 91173x for Japan Patent 118772 (10/18/76).
Derwent Abstract No. 94939x for Japan Patent 125291 (11/1/76).
Derwent Abstract No. 02856y for Japan Patent 136678 (11/26/76).
Derwent Abstract No. 11907y for Japan Patent 000283 (1/5/77).
Derwent Abstract No. 52426c for Japan Patent 076872 (6/10/80).
Derwent Abstract No. 93501e for Japan Patent 154129 (9/22/82).
Derwent Abstract No. 96290e for Japan Patent 159778 (10/1/82).
Derwent Abstract No. 83-786494 for Japan Patent 148817-A (9/5/83).
Derwent Abstract No. 83-786514 for Japan Patent 148861-A (9/5/83).
Derwent Abstract No. 84-168740 for Japan Patent 093-050-A (5/29/84).
Derwent Abstract No. 84-168742 for Japan Patent 093-052-A (5/29/84).

*Primary Examiner*—Donald G. Daus
*Assistant Examiner*—E. Bernhardt
*Attorney, Agent, or Firm*—Brian Lewis; Tom M. Moran; Alan M. Krubiner

[57] ABSTRACT

The invention concerns a method of inhibiting both thromboxane synthetase and cyclic-AMP phosphodiesterase in a mammal having a disease characterized by elevated thromboxane levels or an imbalance of prostacyclin/thromboxane levels with a compound of the formula:

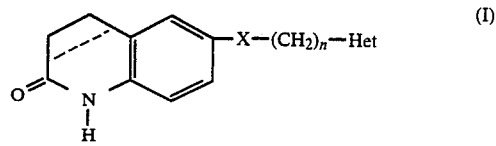

(I)

or a pharmaceutically acceptable acid addition salt or ester thereof, wherein:

X is chosen from the group consisting of:

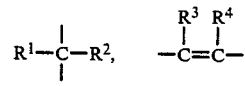

and a covalent bond in which $R^1$ is H, alkyl having 1–6 carbon atoms, optionally substituted phenyl or optionally substituted phenyl lower alkyl, when $R^2$ is H or OH, or $R^1$ and $R^2$ taken together represent oxo, alkylidene having 1–6 carbon atoms or optionally substituted benzylidene;

$R^3$ is H or alkyl having 1–6 carbon atoms, $R^4$ is H and $R^3$ and $R^4$ are either cis or trans to each other, or $R^3$ and $R^4$ taken together represent a covalent bond;

n is an integer from 0–3;

Het is 1-imidazolyl or 3-pyridyl; and the dotted line represents an optional covalent bond.

14 Claims, No Drawings

CARBOSTYRIL DERIVATIVES AS COMBINED THROMBOXANE SYNTHETASE AND CYCLIC-AMP PHOSPHODIESTERASE INHIBITORS

BACKGROUND OF THE INVENTION

1. Field of the Invention

This invention concerns derivatives of carbostyril as agents in the treatment of diseases characterized by an overproduction of thromboxane or an imbalance of thromboxane/prostacyclin, by inhibiting both thromboxane synthetase and cyclic-AMP phosphodiesterase.

2. Related Disclosures

Research work has established that in many tissues the major product of arachidonic acid metabolism by the cyclooxygenase enzyme system is either of two unstable substances, thromboxane $A_2$ ($TxA_2$) or prostacyclin ($PGI_2$). The discovery of $TxA_2$ and $PGI_2$ has significantly increased our understanding of vascular homeostasis. $PGI_2$ for instance is a powerful vasodilator and inhibitor of platelet aggregation, and in this last respect is the most potent endogenous substance so far discovered. The $PGI_2$ synthetase enzyme is located in the endothelial layer of the vasculature, and while it has its own cyclooxygenase system it can utilize endoperoxides released by blood platelets when thromboxane synthetase is inhibited.

$TxA_2$ is synthesized by the thromboxane synthetase enzyme which is located in, for example, the blood platelets. It is a powerful vasoconstrictor and pro-aggregatory substance, the direct opposite functions to those of $PGI_2$. A balance in favor of $PGI_2$ is regarded as beneficial in many conditions such as thrombosis, atherosclerosis, vasospastic cardiovascular disease, diabetes, renal disorders, inflammation, endotoxic shock and possibly even tumor metastasis.

The foregoing demonstrates the desirability of altering the prostacyclin/thromboxane ratio in favor of the former. One method of attempting to achieve this goal is to take advantage of the fact that the immediate precursor to both $PGI_2$ and $TxA_2$ is the same substance, the unstable endoperoxide $PGH_2$. If the synthesis of $TxA_2$ can be blocked, it is then reasonable to expect that more $PGH_2$ will be available for conversion to $PGI_2$. This activity has been demonstrated by several compounds, e.g., dazoxiben, but the levels of prostacyclin thus produced are quite low and may not be therapeutically useful.

Prostacyclin exerts its anti-aggregatory action by elevating cyclic adenosine monophosphate (cyclic-AMP) levels. It is known that cyclic-AMP phosphodiesterase inhibitors, which retard the degradation of cyclic-AMP to the inactive AMP, act synergistically with prostacyclin in elevating cyclic-AMP levels. Thus it is clear that the ability to both inhibit thromboxane synthesis and to inhibit cyclic-AMP phosphodiesterase activity greatly increases the anti-aggregatory potential of a compound. Although both thromboxane inhibitors and cyclic-AMP phosphodiesterase inhibitors are known, the combination of both activities in one compound is novel.

Other carbostyril compounds are described in U.S. Pat. Nos. 3,962,445; 4,309,432; 4,442,106; 4,482,560; 4,487,772; 4,530,930; in Japanese Pat. Nos. J5 5076872; J5-1118772; J5 7159778; and in EP No. 148623. The disclosed compounds are described as having antimicrobial, anti-histaminic, antihypertensive, anti-arhythmic, and cardiotonic activities, to be useful in treating glaucoma and to be inhibitors of blood platelet agglutination and antigen-antibody reactions.

SUMMARY OF THE INVENTION

One aspect of the invention concerns a method of inhibiting both thromboxane synthetase and cyclic-AMP phosphodiesterase in a mammal, particularly a human, having a disease characterized by elevated thromboxane levels or an imbalance of prostacyclin/thromboxane levels which method comprises:

administering to a mammal in need of such a treatment a therapeutically effective amount of a compound of the formula:

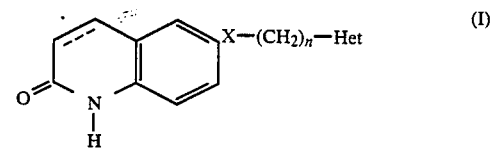

or a pharmaceutically acceptable acid addition salt or ester thereof, wherein:

X is chosen from the group consisting of:

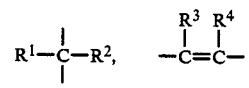

and a covalent bond in which $R^1$ is H, alkyl having 1-6 carbon atoms, optionally substituted phenyl or optionally substituted phenyl lower alkyl, when $R^2$ is H or OH, or $R^1$ and $R^2$ taken together represent oxo, alkylidene having 1-6 carbon atoms or optionally substituted benzylidene;

$R^3$ is H or alkyl having 1-6 carbon atoms, $R^4$ is H and $R^3$ and $R^4$ are either cis or trans to each other, or $R^3$ and $R^4$ taken together represent a covalent bond;

n is an integer from 0-3;

Het is 1-imidazolyl or 3-pyridyl; and the dotted line represents an optional covalent bond.

In another aspect, the invention relates to novel compounds of Formula I, wherein $R^1$, $R^2$, $R^3$, $R^4$, n, X and Het are as defined above with the proviso that when X is a covalent bond and n is 0, Het cannot be 3-pyridyl. Still another aspect is a pharmaceutical composition containing a therapeutically effective amount of a novel compound of Formula I admixed with at least one pharmaceutically acceptable excipient.

Finally, the invention relates to novel processes for preparing the compounds of Formula I, and includes the preparation of several novel intermediates, as discussed hereinafter.

DETAILED DESCRIPTION OF THE INVENTION

Definitions

As used herein:

"Alkyl" means a branched or unbranched saturated hydrocarbon radical containing 1-6 carbon atoms, such as methyl, ethyl, propyl, isopropyl, tert-butyl, butyl, n-hexyl, and the like.

"Alkoxy" means the group -OR wherein R is alkyl as herein defined.

"Alkylidene" means a bivalent radical derived by removal of a hydrogen atom from the monovalent carbon atom of an alkyl group as defined above.

"Phenyl" as used herein encompasses all possible isomeric phenyl radicals optionally monosubstituted with a substituent selected from the group consisting of lower alkyl, lower alkoxy, hydroxy, trifluoromethyl and halogen.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

"Phenyl lower alkyl" means a group in which the optionally substituted phenyl is attached by a methyl, ethyl or propyl, for example benzyl, phenylethyl, 4-chlorophenylpropyl and the like.

"Halo" refers to chloro-, bromo- and iodo-.

The compounds of the invention herein may be converted to an acid addition salt by virtue of the presence of a basic heterocycle. "Pharmaceutically acceptable acid addition salts" refers to those salts which retain the biological effectiveness and properties of the corresponding free bases and which are not biologically or otherwise undesirable. They are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the invention wherein $R^2$ is hydroxy may be converted to an ester with a carboxylic acid, for example, acetic acid, propionic acid, benzoic acid, and the like.

The compounds of this invention are derivatives of "carbostyril", which has the structure shown as Formula II, and has a ring system numbered as shown:

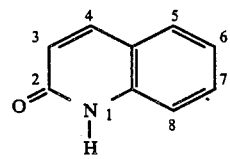

(II)

Following are examples of how representative compounds of Formula I are named using the above shown numbering system:

A compound of Formula I wherein X is $-CR^1R^2-$, wherein $R^1$ is phenyl and $R^2$ is H, n is 0, the optional bond represented by the dotted line is present, and Het is 1-imidazolyl is named "6-[phenyl(imidazol-1-yl)methyl]carbostyril".

A compound of Formula I wherein X is

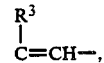

where $R^3$ is methyl, n is 0, the optional bond represented by the dotted line is absent, and Het is 3-pyridyl is named "6-[1-methyl-2-(3-pyridyl)ethenyl]-3,4-dihydrocarbostyril".

A compound of Formula I wherein X is

where $R^3$ and $R^4$ taken together represent a covalent bond, n is 1, Het is 1-imidazolyl, and the optional bond represented by the dotted line is not present, is named "6-[3-(imidazol-1-yl)prop-1-yn-1-yl]-3,4-dihydrocarbostyril".

Although the compounds of Formula I are written in the form of a cyclic amide (as shown above in Formula II) it should be understood that the following tautomerism may occur:

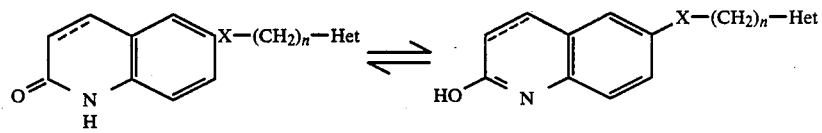

As the carbonyl form is considered the more stable tautomer, the carbostyril derivatives will be named and illustrated as such. However, those skilled in the art will understand that in any particular compound of Formula I both tautomers may be present, and the scope of the claims is intended to embrace all tautomeric forms.

When geometrical isomers are possible, both cis and trans isomers and mixtures thereof fall within the scope of the claims.

Some compounds of Formula I have an asymmetric center. Accordingly, they may be prepared in either optically active form or as a racemic mixture. Unless otherwise specified, the compounds described herein are all racemic mixtures. However, the scope of the invention described and claimed encompasses the individual optical isomers as well as mixtures thereof and the racemic forms of the compounds of Formula I.

If desired, the compounds herein may be resolved into their optical isomers by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula I.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, distillation or a combination of these procedures. Specific illustrations are described in the Examples. However, other equivalent separation or purification procedures can be used.

The salt products are also isolated by conventional means. For example, the reaction mixtures can be evaporated to dryness and the salts then further purified by standard methods such as those listed above.

METHODS OF PREPARATION

The description of the preparation of compounds of Formula 1 is conveniently divided into eight parts.

(a) The compounds of Formula IA are prepared by the procedures illustrated in Reaction Scheme 1.

REACTION SCHEME 1

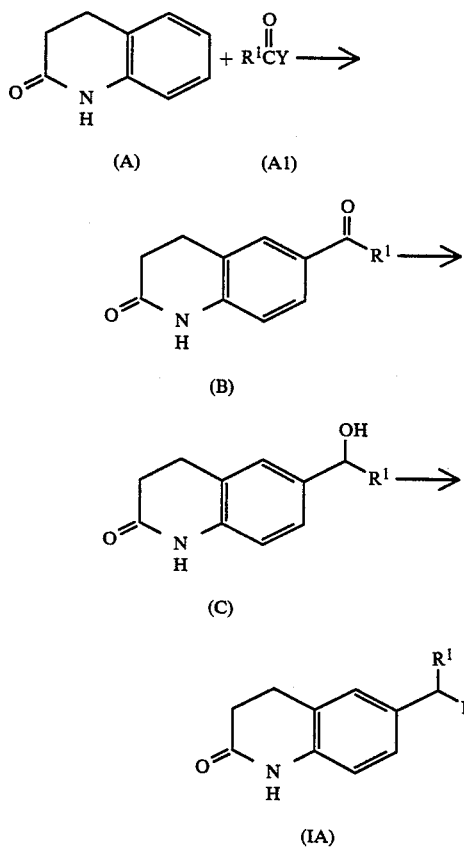

where Y=halo

The compound of Formula A, 3,4-dihydrocarbostyril, is reacted with about 1 to 4 molar equivalents, preferably about 1.5 molar equivalents, of an acyl halide of Formula A1, preferably an acyl chloride, in the presence of about 0.1 to 15 molar equivalents, preferably about 5 to 7 molar equivalents, of a Friedel-Crafts catalyst such as ferric chloride, zinc dichloride, tin tetrachloride, boron trifluoride or preferably aluminum trichloride, in a suitable solvent such as nitromethane, nitrobenzene, acetonitrile, methylene chloride or preferably carbon disulphide. The reaction is conducted at a temperature of about 25°-100° C., preferably about 50° C., for about 1-10 days, preferably about 2 days, giving the compound of Formula B.

The product of Formula B is then reduced with hydrogen and a noble-metal catalyst or with a reducing agent such as aluminum hydride, diborane or preferably sodium borohydride. Typically, the ketone of Formula B is reacted with about 1 to 10 molar equivalents, preferably about 2 to 4 molar equivalents, of sodium borohydride in a protic solvent such as water, ethanol or preferably methanol at a temperature of about 0°-25° C., preferably about 5° C., for about 15 minutes to 40 hours, preferably about 18 hours, giving the compound of Formula C.

Compounds of Formula I

Compounds of Formula IA are obtained by converting the hydroxy moiety in the compound of Formula C into a leaving group, for example by reacting it with a thionyl halide, to convert the hydroxy group into a halide, or reacting it with a sulphonyl halide, for example p-toluenesulphonyl chloride, to give a sulphonate ester. The leaving group is then displaced with imidazole. The preferred method is to treat the compound of Formula C with thionylbis(imidazole), which accomplishes both steps in one reaction. Typically, the compound of Formula C is reacted with about 1 to 4 molar equivalents, preferably about 1.5 molar equivalents, of thionylbis(imidazole) in an inert solvent such as benzene, toluene, acetonitrile, diethyl ether, chloroform, methylene chloride or preferably tetrahydrofuran. The reaction is carried out at a temperature of about 0°-70° C., preferably about 25°, for about 1-40 hours, preferably about 18 hours. When the reaction is substantially complete, the product of Formula IA is isolated by conventional means.

(b) The compounds of Formula IB, IC and ID are prepared by the procedures shown in Reaction Scheme 2.

REACTION SCHEME 2

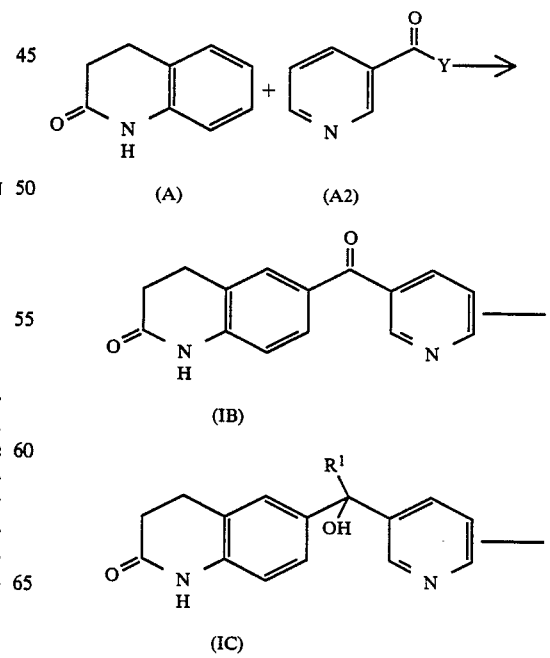

-continued

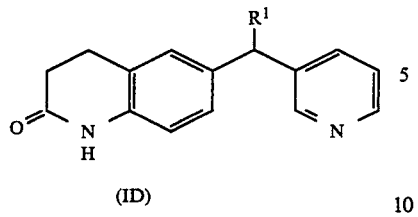

(ID)

The compound of Formula IB is obtained in the same manner as shown for the preparation of the compound of Formula B in section (a) above, substituting a nicotinyl halide of Formula A2 where Y is halo, preferably chloro, for the acyl halide of Formula A1.

The compound of Formula IC, where $R^1$ is H, is obtained in the same manner and under similar conditions as shown for the preparation of the compound of Formula C in section (a) above, i.e. reaction of the ketone of Formula IB with a reducing agent, preferably sodium borohydride.

The compounds of Formula IC, where $R^1$ is other than H, are prepared from the compounds of Formula IB. Typically, the compound of Formula IB is dissolved in an ethereal solvent such as dioxane, tetrahydrofuran or preferably diethyl ether and reacted with about 1 to 5 molar equivalents, preferably about 2 molar equivalents, of an organometallic compound such as an alkyl or aryl lithium or preferably a Grignard reagent of formula $R^1MgY$. The reaction is carried out at a temperature of about 0°–50° C., preferably about 5° C., for about 2–48 hours, preferably about 18 hours. When the reaction is substantially complete, the product of Formula IC is isolated by conventional means.

The compound of Formula IC is then dissolved in an inert solvent as defined above, or methanol or preferably ethanol and reacted with hydrogen at a pressure of about 1–5 atmospheres, preferably about 1 atmosphere, in the presence of a catalyst such as copper chromite, platinum on carbon or preferably palladium on carbon. The reaction is conducted at a temperature of about 0°–50° C., preferably about 25° C., until about 1 molar equivalent of hydrogen is absorbed, typically in about 2 hours. When the reaction is substantially complete, the product of Formula ID is isolated by conventional means.

Alternatively, the compounds of Formula ID are obtained from the compounds of Formula IC by reaction with about 1 to 4 molar equivalents, preferably about 2 molar equivalents, of sodium borohydride in trifluoroacetic acid as a solvent. The reaction is conducted at a temperature of 0°–60° C., preferably about 25° C., for about 30 min. to 8 hours, preferably about 1 hour.

(c) The compounds of Formula IE through IK are prepared as shown in Reaction Scheme 3, where n=1–3, $R^1$ and Het are as defined in the summary and Y is halo.

REACTION SCHEME 3

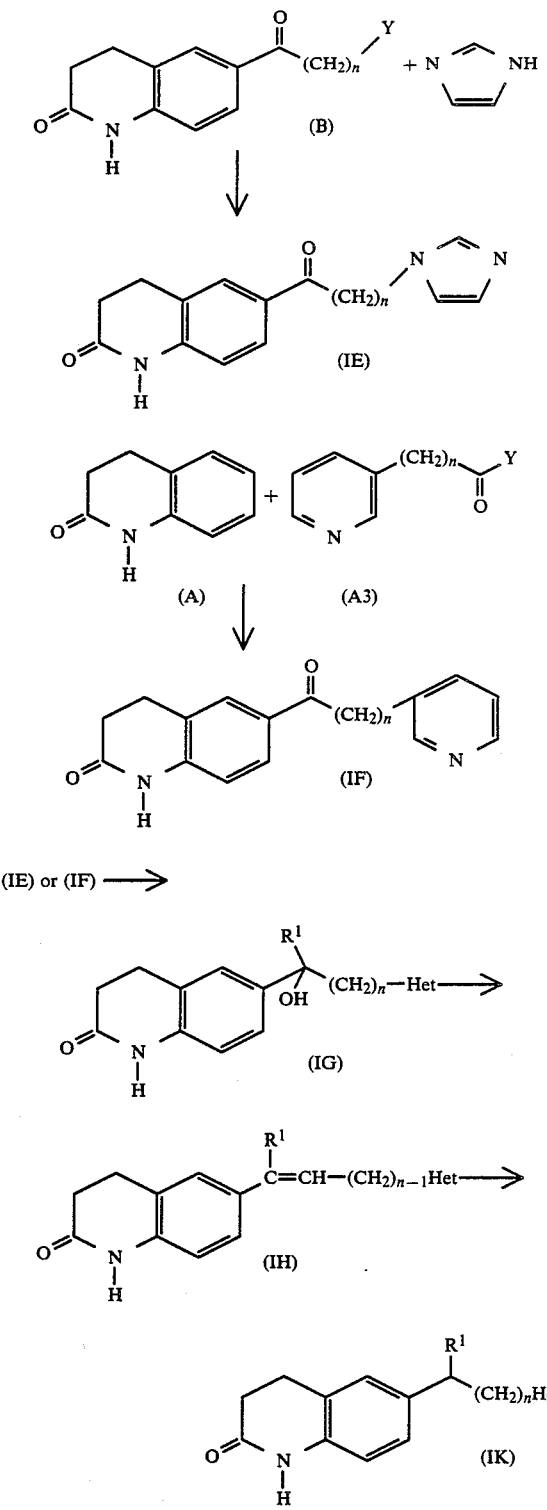

The compound of Formula B, prepared as shown in section (a) above, using a ω-haloacetyl halide in place of $R^1COY$, is reacted with about 2 to 10 molar equivalents, preferably about 4 to 5 molar equivalents, of imidazole in a polar aprotic solvent such as tetrahydrofuran, formamide, dimethyl sulfoxide or preferably N,N-dimethylformamide. The reaction is conducted at a temperature of about 25°-150° C., preferably about 80° C., for about 2-48 hours, preferably about 18 hours. When the reaction is substantially complete, the product of Formula IE is isolated by conventional means.

The compound of Formula IF is obtained in the same manner as shown for the preparation of the compound of Formula IB in section (b) above, substituting the pyridyl ω-acyl halide of Formula A3 for the acyl halide of Formula A2.

The compounds of Formula IG, where $R^1$ is H, are obtained from the compounds of Formula IE or IF in the same manner as shown in section (a) above for the preparation of compounds of Formula C i.e. reaction of the ketones of Formula IE or IF with a reducing agent, preferably sodium borohydride.

An alternative method of making the compound of Formula 1G, where $R^1$ is H, n is 1 and Het is 1-imidazolyl, is from the compound of Formula B of Reaction Scheme 3, where Y is halo. The compound of Formula B is reduced with sodium borohydride as shown above to give the corresponding halohydrin, which is in turn reacted with imidazole, also as shown above, to give the compound of Formula 1G.

The compounds of Formula IG, where $R^1$ is other than H, are prepared from the compounds of Formula IE and IF in the same manner as shown for the preparation of compounds of Formula IC, where $R^1$ is other than H, in section (b) above i.e. reaction of the ketones of Formula IE or IF with an organometallic compound, preferably a Grignard reagent of formula $R^1MgY$, where Y is halo, preferably chloro.

The compounds of Formula IH are prepared from the compounds of Formula IG by reaction with an acid catalyst such as sulfuric acid, phosphorus pentoxide, iodine, zinc chloride or preferably anhydrous formic acid, in an inert solvent as defined above or preferably, where the acid catalyst is a liquid, using the acid as a solvent. Typically, the compound of Formula IG is dissolved in about 1 to 100 molar equivalents, preferably about 20 molar equivalents, of anhydrous formic acid and reacted at a temperature of about 25°-120° C., preferably about 100° C., for about 4-48 hours, preferably about 24 hours. When the reaction is substantially complete, the product of Formula IH is isolated by conventional means.

The compounds of Formula IH are then reacted with hydrogen in the presence of a noble metal catalyst, preferably palladium on carbon, as described for the preparation of compounds of Formula ID in section (b) above, to give the compounds of Formula IK, which are isolated by conventional means.

Alternatively, the compounds of Formula IG can be converted directly to the compounds of Formula 1K as shown in section (b) above for the conversion of the compounds of Formula IC to ID.

(d) The compounds of Formula IL are prepared as shown in Reaction Scheme 4, where $R^0$ is such that $R^0CH_2$ is equivalent to $R^1$ as defined in the summary (not including H), and $R^0CH$ is equivalent to $R^1$ and $R^2$ taken together to represent alkylidene or benzylidene as defined in the summary and n is 0-3 when Het is 3-pyridyl and n is 1-3 when Het is 1-imidazolyl.

REACTION SCHEME 4

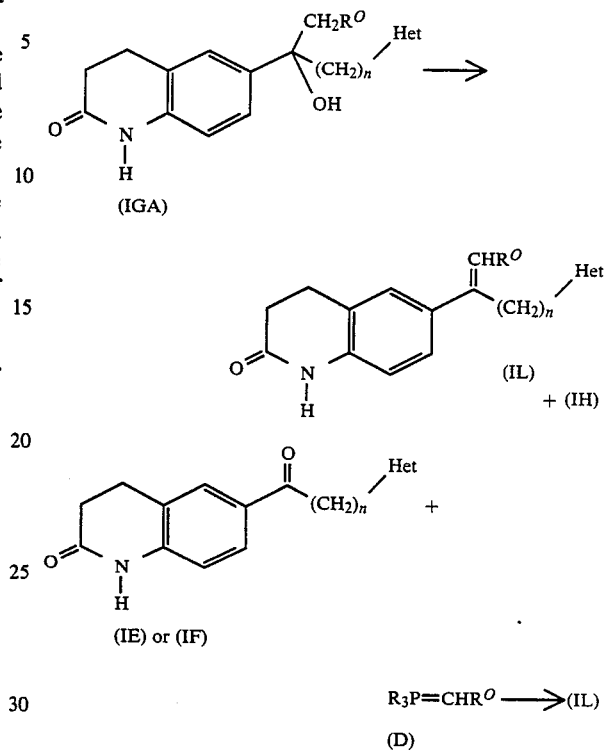

In the method shown for the preparation of compounds of Formula IH, in section (c) above, it should be understood that in compounds of Formula IG where the $R^1$ group contains a CH2 or CH group adjacent to the side chain, (shown as Formula IGA in the above Reaction Scheme 4), acid treatment may lead to a mixture of two distinct isomers, i.e., those of Formula IH and IL. The two isomers are separated by conventional means, giving the compound of Formula IL in a pure form.

Alternatively, the compound of Formula IE or IF is reacted with a phosphorus ylide of Formula D. Typically, the compound of Formula IE or IF is dissolved in an inert solvent as defined above, preferably tetrahydrofuran, and is reacted with about 1 to 4 molar equivalents, preferably about 2.2 molar equivalents, of a compound of Formula D. The reaction is conducted at the temperature of about 0°-80° C., preferably about 40° C., for about 1-40 hours, preferably about 4 hours. When the reaction is substantially complete, the product of Formula IL is isolated by conventional means.

(e) The compounds of Formula IM, IN and IP are prepared as shown in Reaction Scheme 5, where n is 1-3 and Y is halo.

REACTION SCHEME 5

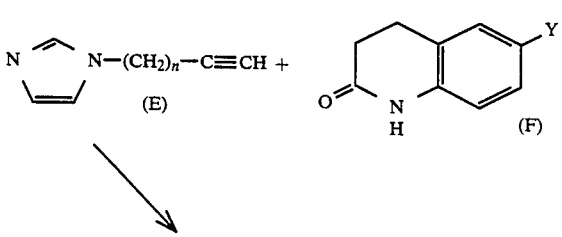

11
-continued

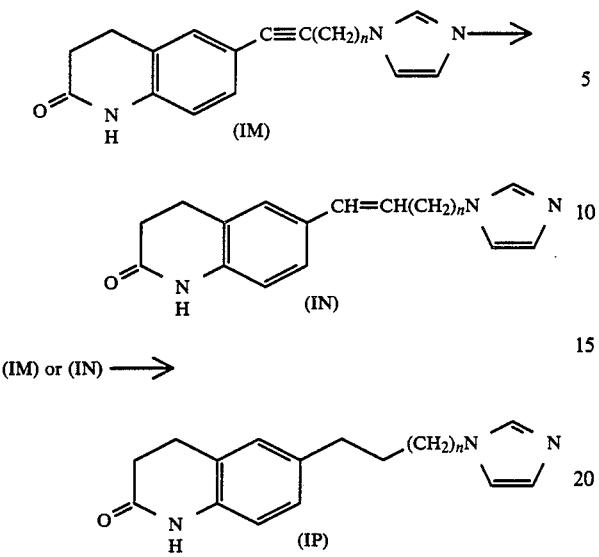

The compound of Formula F, where Y is preferably bromo, is reacted in the presence of about 0.01 to 1.0 molar equivalents, preferably about 0.02 molar equivalents, of a palladium complex, preferably bis(triphenylphosphine)palladium(II)dichloride, and about 0.005 to 0.2 molar equivalents, preferably about 0.01 molar equivalents, of a cuprous halide, preferably cuprous iodide, with about 1.0 to 3.0 molar equivalents, preferably about 1.1 molar equivalents, of the compound of Formula E. The reaction is carried out using a tertiary organic base, such as N-methylpiperidine, triethylamine, pyridine or preferably a mixture of triethylamine and pyridine, as a solvent, at a temperature of about 50°-130° C., preferably about 100° C., for about 1-7 days, preferably about 2 days. When the reaction is substantially complete, the compound of Formula IM is isolated by conventional means.

The compound of Formula IM is then selectively reduced to the olefin of Formula IN by reaction with hydrogen in the presence of a noble metal catalyst, preferably palladium on barium sulphate, mixed with lead acetate, quinoline or preferably pyridine. The hydrogenation is carried out in an inert solvent or a tertiary organic base as defined above, preferably pyridine. Typically, the compound of Formula IM is dissolved in pyridine and from 0.05 to 0.5 molar equivalents, preferably about 0.1 molar equivalents, of palladium on barium sulfate catalyst is added and the mixture is reacted with hydrogen at a pressure of about 1 atmosphere. The reaction is conducted at a temperature of 0°-50° C., preferably about 25° C., until 1 molar equivalent of hydrogen has been absorbed, typically about 2 hours. When the reaction is substantially complete, the compound of Formula IN is isolated by conventional means.

The compound of Formula IP is made by hydrogenation of the compound of Formula IM or IN in the same manner as shown for the preparation of compounds of Formula IK in section (c) above, carrying out the reaction until the theoretical amount of hydrogen is absorbed. When the reaction is substantially complete, the compound of Formula IP is isolated by conventional means.

(f) The compound of Formula IQ is prepared as shown in Reaction Scheme 6.

12
REACTION SCHEME 6

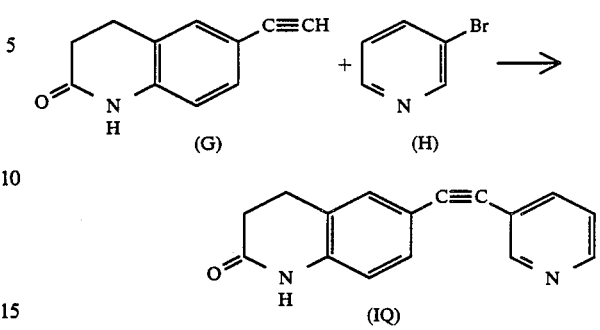

The compound of Formula IQ is made in the same manner as shown for the preparation of the compound of Formula IM in section (e) above, substituting the compounds of Formula G and H for the compounds of Formula F and E respectively.

(g) The compounds of Formula IR and IS are prepared as shown in Reaction Scheme 7, where Y is halo.

REACTION SCHEME 7

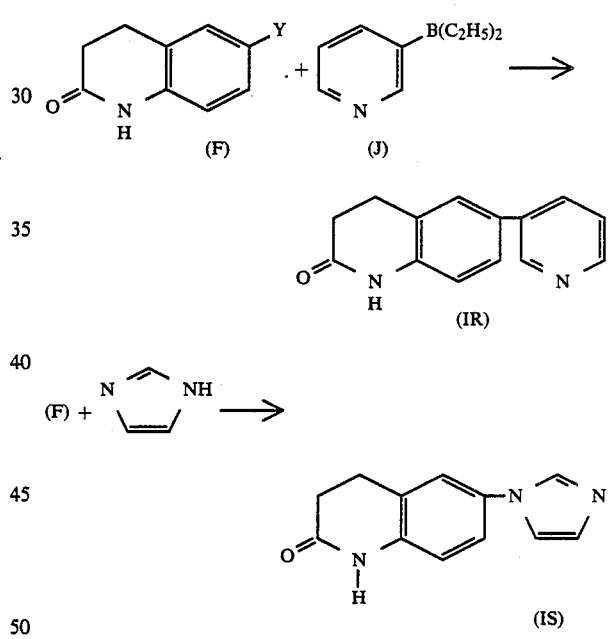

The compound of Formula IR is prepared from the compound of Formula F, where Y is preferably bromo, by reaction with about 2 to 6 molar equivalents, preferably about 2.5 molar equivalents, of powdered potassium hydroxide and about 0.05 to 0.2 molar equivalents, preferably about 0.1 molar equivalents, of a quaternary ammonium salt, such as tetraethylammonium chloride, benzyltrimethylammonium hydroxide or preferably tetrabutylammonium bromide together with about 0.5 to 3 molar equivalents, preferably about 0.8 molar equivalents, of the compound of Formula J. The reaction is carried out in the presence of about 0.01 to 1.0 molar equivalents, preferably about 0.03 molar equivalents, of tetrakis(triphenylphosphine)palladium, in an inert organic solvent as defined above, preferably tetrahydrofuran. The reaction is conducted at a temperature of about 25°-100° C., preferably about 65° C., for about 1-7 days, preferably about 2 days. When the reaction is substantially complete, the compound of Formula IR is isolated by conventional means.

The compound of Formula IS is also prepared from the compound of Formula F, where Y is preferably bromo, by reaction with about 1-5 molar equivalents, preferably about 1.2 molar equivalents, of imidazole in the presence of about 0.01 to 0.1 molar equivalents, preferably about 0.05 molar equivalents, of cuprous iodide and about 1-5 molar equivalents, preferably about 1.2 molar equivalents, of potassium carbonate in a polar aprotic solvent as defined above, preferably N,N-dimethylformamide. The reaction is carried out at a temperature of about 40°-120° C., preferably about 90° C., for 1-7 days, preferably about 2 days. When the reaction is substantially complete, the compound of Formula IS is isolated by conventional means.

(h) The compounds of Formula IU are prepared as shown in Reaction Scheme 8, where X, n and Het are as defined in the summary.

REACTION SCHEME 8

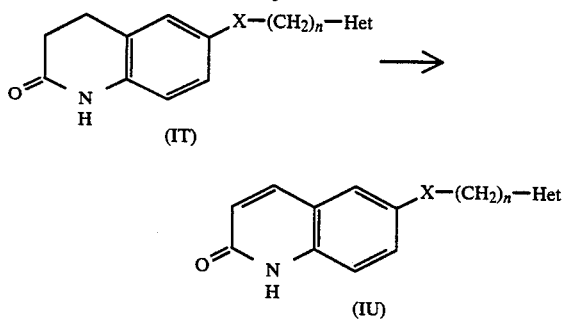

The 3,4-dihydrocarbostyril derivative of Formula IT, prepared by any of the methods shown in Reaction Schemes 1-7, is dissolved in a polar aprotic solvent as defined above, preferably N,N-dimethylformamide, and reacted with about 2 to 20 molar equivalents, preferably about 8 molar equivalents, of an oxidizing agent such as a benzoquinone, for example 2,3-dichloro-5,6-dicyanobenzoquinone, or agents capable of producing the same result such as N-bromosuccinimide, or palladium on carbon, palladium oxide, Raney nickel or the like, or preferably nickel peroxide. The reaction is conducted at a temperature of about 0°-50° C., preferably about 25° C., for about 1-7 days, preferably about 3 days. When the reaction is substantially complete, the compound of Formula IU is isolated by conventional means.

Salts of Compounds of Formula I

The compounds of Formula I may be converted to their acid addition salts by virtue of the presence of the basic heterocycle.

The compound of Formula I in free base form may be converted to the acid addition salts by treating with a stoichiometric excess of the appropriate organic or inorganic acid, such as, for example, oxalic, citric, malonic, (+)-tartaric, (±)-lactic, phosphoric, hydrochloric or sulfuric acid and the like. Typically, the free base is dissolved in a polar organic solvent such as ethanol or methanol, and the acid added thereto. The temperature is maintained between about 0° C. and 50° C. The resulting acid addition salt precipitates spontaneously or may be brought out of solution with a less polar solvent.

The acid addition salts of the compounds of Formula I may be decomposed to the corresponding free base by treating with a stoichiometric amount or an excess of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and boiling point of the solvent being used as the medium for the procedure.

Preparation of Starting Materials

The compounds of Formula I are prepared from 3,4-dihydrocarbostyril of Formula A, which is prepared as shown in Preparation 1.

The acyl halides of Formulae A1, A2 and A3 are prepared from the commercially available carboxylic acids by procedures well known to those skilled in the art. For example, to prepare the compound of Formula A1 where Y is chloro, the appropriate carboxylic acid is reacted with thionyl chloride or oxalyl chloride. The reaction is discussed in more detail in *Comprehensive Organic Chemistry*, Vol. 2, by Barton and Ollis, pp. 633-634, which is incorporated herein by reference.

The Grignard reagents of Formula $R^1MgY$ are commercially available. Alternatively, they can be prepared by standard methods, for example, by treating the appropriate halide of formula $R^1Y$ with magnesium. The reaction is discussed in more detail in *Comprehensive Organic Chemistry*, Vol. 3, by Barton and Ollis, pp 972-985, which is incorporated herein by reference.

The phosphorus ylides of Formula D (Wittig reagents) are prepared by procedures well known in the chemical arts. For example, by reaction of the appropriate halide of formula $R^1CH_2Y$ with triphenylphosphine followed by treatment of the resultant phosphonium salt with a base. The reaction is discussed in more detail in *Comprehensive Organic Chemistry*, Vol. 1, by Barton and Ollis, pp 136-139, which is incorporated herein by reference.

The compound of Formula F, 6-halo-3,4-dihydrocarbostyril, is prepared by standard procedures. For example, by reaction of 3,4-dihydrocarbostyril with N-bromosuccinimide. The reaction is discussed in more detail in the *Journal of Organic Chemistry*, Vol. 30, pp 3163-3166, which is incorporated herein by reference.

The compound of Formula J, 3-pyridyldiethylborane, is prepared by procedures well known in the chemical arts. For example, reaction of 3-bromopyridine with butyl lithium followed by triethylborane and quenching with iodine gives the desired compound of Formula J. The reaction is discussed in more detail in the *Chemical and Pharmaceutical Bulletin*, Vol. 31, pp 4573-4577, which is incorporated herein by reference.

In summary, the compounds of the present invention are made by the procedures below:

(1) A process for the preparation of a compound of Formula IU wherein:

X is chosen from the group consisting of:

$$R^1-\underset{|}{\overset{|}{C}}-R^2, \quad -\underset{|}{\overset{R^3}{C}}=\underset{|}{\overset{R^4}{C}}-$$

and a covalent bond in which

R¹ is H, alkyl having 1–6 carbon atoms, optionally substituted phenyl or optionally substituted phenyl lower alkyl, when R² is H or OH, or R¹ and R² taken together represent oxo, alkylidene having 1–6 carbon atoms or optionally substituted benzylidene;

R³ is H or alkyl having 1–6 carbon atoms, R⁴ is H, and R³ and R⁴ are either cis or trans to each other, or R³ and R⁴ taken together represent a covalent bond;

n is an integer from 0–3;

Het is 1-imidazolyl or 3-pyridyl; and the optional bond, represented by the dotted line is present, which process comprises:

reacting a compound of the formula

<chemical structure: 3,4-dihydrocarbostyril with X—(CH₂)ₙ—Het substituent at 6-position> where X, n and Het are as defined above, with an oxidizing agent to form a compound of Formula I wherein the optional covalent bond represented by the dotted line is present, or (2) The process for preparing the compounds of Formula IA comprises reacting a compound of the formula <chemical structure: 3,4-dihydrocarbostyril with CH(L)(R¹) substituent at 6-position> wherein R¹ is as defined above and L is hydroxy, with (a) thionylbis(imidazole), or alternatively where L is a leaving group, with (b) imidazole or a salt or derivative thereof.

(3) The process for preparing the compounds of Formula IB and IF comprises:

reacting a compound of the formula

<chemical structure: 3-pyridyl-(CH₂)ₙ-C(=O)-Y> where Y is a halogen and n=0–3 with 3,4-dihydrocarbostyril and a Friedel-Crafts catalyst.

(4) The process for preparing the compounds of Formula IC and IG where R¹ is H comprises reacting a compound of the formula <chemical structure: 3,4-dihydrocarbostyril with C(=O)—(CH₂)ₙ—Het at 6-position> where n=0–3 when Het is 3-pyridyl and n=1–3 when Het is 1-imidazolyl, with a reducing agent such as sodium borohydride.

(5) An alternative process for preparing the compound of Formula IG where R¹ is H, n is 1 and Het is 1-imidazolyl comprises reacting a compound of the formula <chemical structure: 3,4-dihydrocarbostyril with C(=O)—CH₂—Y at 6-position> where Y is halogen, with sodium borohydride, optionally converting the product to an epoxide followed by reaction with imidazole or a salt or derivative thereof.

(6) The process for preparing compounds of Formula IC and IG, wherein R¹ is alkyl having 1–6 carbon atoms, optionally substituted phenyl or optionally substituted phenalkyl comprises reacting a compound of the formula <chemical structure: 3,4-dihydrocarbostyril with C(=O)—(CH₂)ₙ—Het at 6-position> where n=0–3 when Het is 3-pyridyl and n=1–3 when Het is 1-imidazolyl, with a Grignard reagent of formula R¹MgY, where Y is halogen and R¹ is as defined in the summary, or an organometallic compound of formula R¹M where M is a metal.

(7) The process for preparing the compounds of Formula ID comprises reacting a compound of the formula <chemical structure: 3,4-dihydrocarbostyril with C(R¹)(OH)-3-pyridyl at 6-position> where R¹ is as defined in the summary, with (a) hydrogen in the presence of a noble metal catalyst, or (b) sodium borohydride and trifluoroacetic acid.

(8) The process for preparing the compounds of Formula IE comprises reacting a compound of the formula

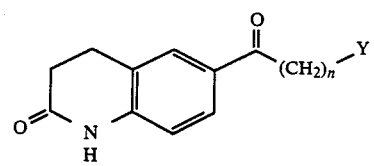

where Y is halogen and n=1-3, with imidazole.

(9) The process for preparing the compounds of Formula IH, comprises reacting a compound of the formula

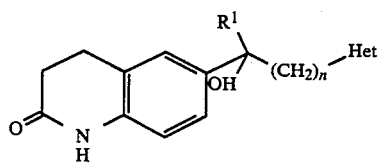

where R¹ and Het are as defined in the summary and n=1-3, with an acid catalyst.

(10) The process for preparing compounds of Formula IK comprises reacting a compound of the formula

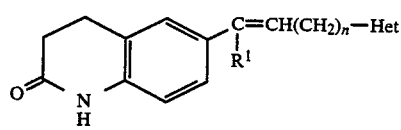

where R¹ and Het are as defined in the summary and n=0-2, with hydrogen and a noble metal catalyst.

(11) The process for preparing the compounds of Formula IL comprises reacting a compound of the formula

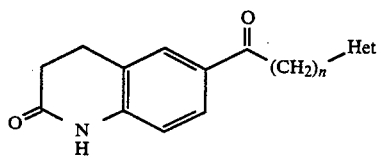

where n=0-3 when Het is 3-pyridyl and n=1-3 when Het is 1-imidazolyl, with a phosphorus ylide of Formula $(R)_3P=CHR^0$, where (R) is alkyl or aryl and $R^0$ is as defined in section (d) above.

(12) Alternatively, the process for preparing the compounds of Formula IL comprises reacting a compound of the formula

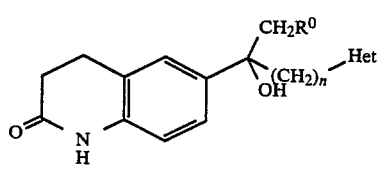

where $R^0$ is as defined above and n=0-3 when Het is 3-pyridyl and n=1-3 when Het is 1-imidazolyl, with an acid catalyst.

(13) The process for preparing the compound of Formula IM comprises reacting a compound of the formula

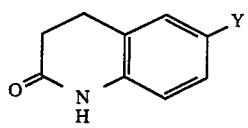

where Y is halo, with a compound of the formula

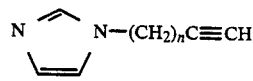

where n is 1-3, in the presence of a palladium complex and optionally a copper(I) salt.

(14) The process for preparing the compounds of Formula IH, where R¹ is H, and IN comprises reacting a compound of the formula

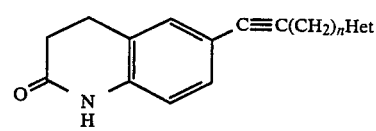

where n=0-3 when Het is 3-pyridyl and n=1-3 when Het is 1-imidazolyl, with hydrogen and a suitable palladium catalyst until 1 molar equivalent of hydrogen is absorbed.

(15) The process for preparing the compounds of Formula IK, where R¹ is H, and Formula IP comprises reacting a compound of the formula

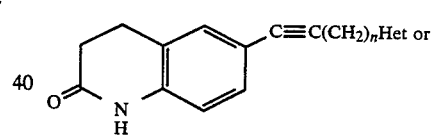

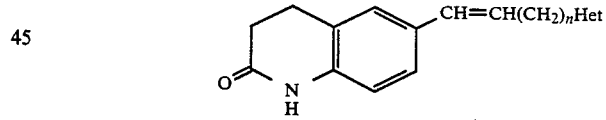

where n=0-2 when Het is 3-pyridyl and n=1 or 2 when Het is 1-imidazolyl, with hydrogen and a noble metal catalyst.

(16) The process for preparing the compound of Formula IQ comprises reacting a compound of the formula

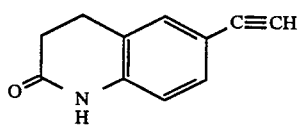

with 3-bromopyridine in the presence of a palladium (II) complex and optionally a copper(I) halide.

(17) A process for the preparation of compounds of Formula IR comprises reacting a compound of the formula

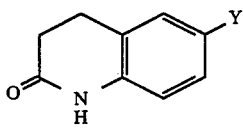

where Y is halo, with 3-pyridyldiethylborane in the presence of a base, a quarternary ammonium halide and a palladium(O) complex.

(18) The process for the preparation of compounds of Formula IS comprises reacting a compound of the formula

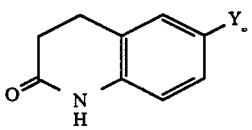

where Y is halo, with imidazole in the presence of cuprous iodide and a base.

(19) The process for the preparation of a pharmaceutically acceptable acid addition salt of a compound of Formula I, or the conversion of an acid addition salt of a compound of Formula I to the free base comprises (a) reacting the free base of the compound of Formula I with an acid to form the corresponding pharmaceutically acceptable salt; or (b) reacting the acid addition salt of the compound of Formula I with a base, to form the corresponding free base; or (c) converting an acid addition salt of the compound of Formula I to another pharmaceutically acceptable acid addition salt.

Utility and administration

The compounds of Formula I have been shown in standard laboratory tests to be useful in treating diseases characterized by elevated thromboxane levels or an imbalance of prostacyclin/thromboxane in mammals. Accordingly, the compounds of Formula I, their salts and pharmaceutical compositions containing them, may be used in treating such disease states in mammals by administering a therapeutically effective amount of a compound of Formula I to a mammal in need of such a treatment. In addition to altering the prostacyclin/thromboxane ratio and lowering thromboxane levels, the compounds of Formula I operate by a novel mode of action to simultaneously elevate intracellular cyclic-AMP. The outcome of this is a much more pronounced effect than a compound with either mode of action singly, and an effect similar to that which would normally require much greater elevations of prostacyclin. The inhibition of thromboxane synthesis was determined by measurement of the ability to inhibit human platelet aggregation by ADP as described in Example 24 below. The inhibition of cyclic-AMP phosphodiesterase activity was determined by the method described in Example 25 below.

Administration of the active compounds and salts described herein may be effected via any medically accepted mode of administration for agents which control thromboxane synthesis, cyclic-AMP phosphodiesterase activity, platelet aggregation or associated activities.

These methods include but are not limited to oral, parenteral, topical and otherwise systemic routes of administration. Oral administration is preferred, depending of course, on the disorder being treated. The compounds are administered in a therapeutically effective amount either alone or in combination with a suitable pharmaceutically acceptable excipient.

Depending on the intended mode of administration, the compounds of this invention may be incorporated in any pharmaceutically acceptable dosage form, such as, for example, tablets, suppositories, pills, capsules, powders, liquids, suspensions, emulsions, aerosols, or the like. Preferable means of administration are unit dosage forms suitable for single administration of precise dosages, or sustained release dosage forms for continuous administration. Preferably the dosage form will include a pharmaceutically acceptable excipient and an active compound of Formula I, or a pharmaceutically acceptable salt thereof, and, in addition, may include other medicinal agents, pharamceutical agents, carriers, excipients, adjuvants, stabilizers, etc. Depending on parameters such as mode of administration, type of composition, and activity of the compound, the pharmaceutical composition may contain 1–95 percent by weight active ingredient, preferably 25–70 percent, with the remainder being excipient.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose, and magnesium carbonate. An example of a solid dosage form of the compounds of this invention is a suppository containing propylene glycol as the carrier. Liquid pharmaceutically administerable dosage forms can, for example, comprise a solution or suspension of an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slowrelease or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.5%–10%; preferably 1–2%.

For oral administration, a pharmaceutically acceptable non-toxic dosage form may contain any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such dosage forms may contain 1%–95% active ingredient, preferably 25–70%.

The amount of active compound administered will, of courese, depend on the subject being treated, the severity of the affliction, the manner of administration and the judgment of the prescribing physician. However, a therapeutically effective dosage of compounds of the instant invention is in the range of 1–100 mg/kg/day, preferably about 5–30 mg/kg/day, and most preferably about 10 mg/kg/day. For an average 70 kg human, this would amount to 70 mg–7 g per day, or preferably about 700 mg/day.

Preferred Embodiments

Among the family of compounds of the present invention, one preferred group includes those compounds of Formula I in which Het is 3-pyridyl. (1) One preferred embodiment of this group concerns compounds of Formula I wherein X is $-CR^1R^2$ and is 0 or 1. Within this subgroup one preferred subclass includes compounds of Formula I in which $R^1$ and $R^2$ taken together represents oxo. A second preferred subclass within this subgroup includes compounds of Formula I in which $R^1$ is H, lower alkyl having 1–3 carbon atoms or optionally substituted phenyl and $R^2$ is OH. A more preferred subclass includes compounds of Formula I in which $R^1$ is phenyl and $R^2$ is H, especially where n is 0 and the optional bond represented by the dotted line is absent. (2) A second preferred embodiment of this group concerns compounds of Formula I in which X is

and n is 0 or 1. Within this subgroup one preferred subclass includes compounds of Formula I in which $R^3$ and $R^4$ taken together represent a covalent bond. A second preferred subclass within this subgroup includes compounds of Formula I in which $R^3$ is H or alkyl and $R^4$ is H.

A second preferred group consists of compounds of Formula I in which Het is 1-imidazolyl. (1) One preferred embodiment of this group concerns compounds of Formula I wherein X is $-CR^1R^2$. Within this subgroup one preferred subclass includes compounds of Formula I wherein $R^1$ and $R^2$ taken together represent alkylidene having 1–3 carbon atoms. A second preferred subclass concerns those compounds of Formula I in which $R^1$ is alkyl or phenyl, $R^2$ is H and n is 0, especially where $R^1$ is phenyl and the optional bond represented by the dotted line is present or absent, or where $R^1$ is alkyl and the optional bond represented by the dotted line is absent. (2) A second preferred embodiment concerns those compounds of Formula I wherein X is a covalent bond and the optional bond represented by the dotted line is absent. Particularly preferred among this subgroup are those compound of Formula I in which n is 0 or where n is 3. (3) A third preferred embodiment concerns compounds of Formula I wherein X is

and n is 0 or 1. Within this subgroup, one preferred subclass includes compounds of Formula I where $R^3$ and $R^4$ taken together is a covalent bond. A second preferred subclass concerns those compounds of Formula I wherein $R^3$ is H or lower alkyl having 1–3 carbon atoms and $R^4$ is H. Particularly preferred among this second subgroup are those compounds where $R^3$ is methyl, n is 0 and the optional bond represented by the dotted line is absent, and where $R^3$ is H, n is 0 and the optional bond represented by the dotted line is present or absent, and where $R^3$ is H, n is 1 and the optional bond represented by the dotted line is absent.

At present, the most preferred compounds of Formula I are:
6-[phenyl(3-pyridyl)methyl]-3,4-dihydrocarbostyril;
6-[phenyl(imidazl-1-yl)methyl]-3,4-dihydrocarbostyril;
6-[phenyl(imidazol-1-yl)methyl]carbostyril;
6-[1-(imidazol-1-yl)hexyl]-3,4-dihydrocarbostyril;
6-(imidazol-1-yl)-3,4-dihydrocarbostyril;
6-[1-methyl-2-(imidazol-1-yl)ethenyl]-3,4-dihydrocarbostyril;
6-[2-(imidazol-1-yl)ethenyl]-3,4-dihydrcarbostyril;
6-[3-(imidazol-1-yl)prop-1-en-1-yl]-3,4-dihydrocarbostyril;
6-[3-(imidazol-1-yl)propyl]-3,4-dihydrocarbostyril; and
6-[2-(imidazol-1-yl)ethenyl]carbostyril.

The following preparations and examples serve to illustrate the invention. They are simply representative and should not be construed as in any way narrowing or limiting the scope of the invention as claimed.

PREPARATION 1

Preparation of 3,4-dihydrocarbostyril

A solution of 25 g of o-nitrocinnamic acid in 250 ml of ethanol was shaken with 2.5 g of 10% palladium on carbon under hydrogen at a pressure of 3 atmospheres. When the theoretical amount of hydrogen had been absorbed the catalyst was filtered off, washed with hot ethanol and the filtrate evaporated under reduced pressure to give 3,4-dihydrocarbosytril, m.p. 168°–169° C.

PREPARATION 2

Preparation of 6-ethynyl-3,4-dihydrocarbostyril

A mixture of 8.0 g of 6-bromo-3,4-dihydrocarbostyril, 6.95 g of trimethylsilylacetylene, 460 mg of bis(triphenylphosphine)palladium dichloride and 62 mg of cuprous iodide in 53 ml of pyridine and 11 ml of triethylamine was refluxed for 3 days. The solvent was removed under reduced pressure, 50 ml of methanol added along with 300 mg of potassium carbonate, and the mixture stirred under nitrogen for 18 hours. The solvent was removed under reduced pressure and the residue chromatographed on silica gel, eluting with 3% methanol in methylene chloride, giving a product of 6-ethynyl-3,4-dihydrocarbostyril, m.p. 182°–184° C.

PREPARATION 3

Preparation of 1-propargylimidazole (a) To a solution of 14 g of 1-trimethylsilylimidazole in 60 ml of acetonitrile was added 11.9 g of propargyl bromide, and the mixture refluxed for 18 hours. To the cooled solution was added 20 ml of methanol followed by 14 ml of triethylamine. The solvent was removed under reduced pressure and the residue stirred with 100 ml of tetrahydrofuran and filtered. The solvent was removed from the filtrate under reduced pressure and the residue chromatographed on silica gel, eluting with 5% methanol in methylene chloride, giving 1-propargylimidazole.

1H NMR (CDCl$_3$), δ 2.51 (t, 1H, J=2.6 Hz), 4.71 (d, 2H, J=2.3 Hz), 7.01 (s, 1H), 7.05 (s, 1H), 7.55 (s, 1H).

(b) Similarly, starting with the appropriate ω-haloalk-1-yne, the following compounds are prepared:
1-(but-3-ynyl)imidazole; and
1-(pent-4-ynyl)imidazole.

PREPARATION 4

Preparation of 6-benzoyl-3,4-dihydrocarbostyril and related compounds of Formula B (a) A mixture of 2.2 g of 3,4-dihydrocarbostyril, 3.21 g of benzoyl chloride and 13 g of aluminum chloride in 50 ml of carbon disulfide was refluxed for 2 days. The reaction mixture was poured onto ice water and the resulting solid filtered off, washed with water and dried under reduced pressure to yield 6-benzoyl-3,4-dihydrocarbostyril, m.p. 205°–207° C.

(b) Similarly, following the procedures of part (a) above, starting with the appropriate acyl halides of Formula A1 in place of benzoyl chloride, the following compounds of Formula B were prepared:
6-acetyl-3,4-dihydrocarbostyril, m.p. 162°–163°
6-hexanoyl-3,4-dihydrocarbostyril, m.p. 145°–147° C., and
6-chloroacetyl-3,4-dihydrocarbostyril, m.p. 224°–226°

(c) The following compounds of Formula B are similarly prepared following the procedures of part (a) above,:
6-propanoyl-3,4-dihydrocarbostyril;
6-butanoyl-3,4-dihydrocarbostyril;
6-isobutanoyl-3,4-dihydrocarbostyril;
6-n-pentanoyl-3,4-dihydrocarbostyril;
6-n-heptanoyl-3,4-dihydrocarbostyril;
6-(2-chlorobenzoyl)-3,4-dihydrocarbostyril;
6-(4-chlorobenzoyl)-3,4-dihydrocarbostyril;
6-(4-methoxybenzoyl)-3,4-dihydrocarbostyril;
6-(2,4-dimethylbenzoyl)-3,4-dihydrocarbostyril; and
6-phenylacetyl-3,4-dihydrocarbostyril.

PREPARATION 5

Preparation of 6-(phenylhydroxymethyl)-3,4-dihydrocarbostyril and related compounds of Formula C (a) A suspension of 3.0 g of 6-benzoyl-3,4-dihydrocarbostyril in 120 ml of methanol was treated at 0° C. with 1.2 g of sodium borohydride. The mixture was stirred at 25° C. for 18 hours during which time the suspended solid dissolved. The solvent was removed under reduced pressure and the residue partitioned between 10% methanol in methylene chloride and water. The extract was dried over anhydrous sodium sulfate, filtered and the solvent removed under reduced pressure. The residue was recrystallized from ethanol to give 6-(phenylhydroxymethyl)-3,4-dihydrocarbostyril, m.p. 166°–169° C.

(b) Similarly, starting with the appropriate compounds of Formula B in place of 6-benzoyl-3,4-dihydrocarbostyril and following the procedures of part (a) above, the following compounds of Formula C were prepared:
6-(1-hydroxyethyl)-3,4-dihydrocarbostyril, m.p. 173°–175° C. and
6-(1-hydroxyhexyl)-3,4-dihydrocarbostyril, m.p. 111°–112° C.

(c) Similarly, following the procedures of part (a) above, the following compounds of Formula C are prepared:
6-(1-hydroxypropyl)-3,4-dihydrocarbostyril;
6-(1-hydroxy-n-butyl)-3,4-dihydrocarbostyril;
6-(1-hydroxyisobutyl)-3,4-dihydrocarbostyril;
6-(1-hydroxy-n-pentyl)-3,4-dihydrocarbostyril;
6-(1-hydroxy-n-heptyl)-3,4-dihydrocarbostyril;
6-(1-hydroxy-2-phenylethyl)-3,4-dihydrocarbostyril;
6-[1-hydroxy(2-chlorophenyl)methyl]-3,4-dihydrocarbostyril;
6-[1-hydroxy(4-chlorophenyl)methyl]-3,4-dihydrocarbostyril;
6-[1-hydroxy(4-methoxyphenyl)methyl]-3,4-dihydrocarbostyril; and
6-[1-hydroxy(2,4-dimethylphenyl)methyl]-3,4-dihydrocarbostyril.

EXAMPLE 1

Preparation of 6-[phenyl(imidazol-1-yl)methyl]-3,4-dihydrocarbostyril and related compounds of Formula IA (a) A freshly prepared solution of thionylbis(imidazole) was prepared by adding 1.19 g of thionyl chloride to a solution of 2.72 g of imidazole in 30 ml of tetrahydrofuran at 0° C., stirring for 30 minutes at 25° C. then filtering. A solution of 1.7 g of 6-[phenyl(hydroxy)methyl]-3,4-dihydrocarbostyril in 5 ml of tetrahydrofuran was added to the filtrate at 0° C., then the solution was stirred at 25° C. for 18 hours. The solvent was removed under reduced pressure, the residue partitioned between 10% methanol in methylene chloride and water and the organic solution separated and dried over anhydrous sodium sulfate. The mixture was filtered, solvent removed from the filtrate under reduced pressure and the residue chromatographed on silica gel, eluting with 3% methanol in methylene chloride, affording 6-[phenyl(imidazol-1-yl)methyl]-3,4-dihydrocarbostyril, m.p. 215°–217° C.

(b) Following the procedure described in paragraph (a) above, but starting with the appropriate compounds of Formula C, synthesized according to the method in Preparation 2, the following compounds of Formula IA were prepared:
6-[1-(imidazol-1-yl)ethyl]-3,4-dihydrocarbostyril, m.p. 173°–175° C.; and
6-[1-(imidazol-1-yl)hexyl]-3,4-dihydrocarbostryil, m.p. 137°–141° C.

(c) In a similar manner, following the procedure described in paragraph (a) above, the following compounds of Formula IA are prepared:
6-[1-(imidazol-1-yl)propyl]-3,4-dihydrocarbostyril;

6-[1-(imidazol-1-yl)butyl]-3,4-dihydrocarbostyril;
6-[1-(imidazol-1-yl)isobutyl]-3,4-dihydrocarbostyril;
6-[1-(imidazol-1-yl)pentyl]-3,4-dihydrocarbostyril;
6-[1-(imidazol-1-yl)heptyl]-3,4-dihydrocarbostyril;
6-[1-(imidazol-1-yl)-2-phenylethyl]-3,4-dihydrocarbostyril;
6-[(imidazol-1-yl)(2-chlorophenyl)methyl]-3,4-dihydrocarbostyril;
6-[(imidazol-1-yl)(4-chlorophenyl)methyl]-3,4-dihydrocarbostyril;
6-[(imidazol-1-yl)(4-methoxyphenyl)methyl]-3,4-dihydrocarbostyril; and
6-[(imidazol-1-yl)(2,4-dimethylphenyl)methyl]-3,4-dihydrocarbostryil.

EXAMPLE 2

Preparation of 6-[(Imidazol-1-yl)acetyl]-3,4-dihydrocarbostyril the compound of Formula IE (a) A solution of 9.0 g of 6-(chloroacetyl)-3,4-dihydrocarbostyril and 13.4 g of imidazole in 40 ml of N,N-dimethylformamide was heated at 80° C. for 18 hours. The reaction mixture was diluted with 1000 ml of water and the precipitate filtered off, washed with water followed by a little acetone and dried under vacuum to afford 6-[(imidazol-1-yl)acetyl]-3,4-dihydrocarbostyril, having a melting point of 269°–273° C.

(b) Similarly, starting with the appropriate haloketone of Formula B (where $R^1$ is $(CH_2)_nY$) in place of 6-(chloroacetyl)-3,4-dihydrocarbostyril, and following the procedure described in paragraph (a) above, the following compounds of Formula IE are prepared:
6-[1-oxo-2-(imidazol-1-yl)ethyl]-3,4-dihydrocarbostyril; and
6-[1-oxo-3-(imidazol-1-yl)propyl]-3,4-dihydrocarbostyril.

EXAMPLE 3

Preparation of 6-(3-pyridylcarbonyl)-3,4-dihydrocarbostyril and related compounds of Formula IB and IF (a) A mixture of 1.42 g of nicotinoyl chloride (a compound of Formula A2), 6 g of aluminum trichloride and 1 g of 3,4-dihydrocarbostyril were reacted in the same manner as in Preparation 1. The product was isolated similarly giving 6-(3-pyridylcarbonyl)-3,4-dihydrocarbostyril, m.p. 195°–202° C.

(b) Following the procedure described in paragraph (a) above, but starting with 3-pyridylacetyl chloride as the compound of Formula A2, the following compound of Formula IF was prepared:
6-(3-pyridylacetyl)-3,4-dihydrocarbostyril m.p. 207°–209° C.

(c) Similarly, the following compounds of formula IF are prepared:
6-[3-(3-pyridyl)propanoyl]-3,4-dihydrocarbostyril; and
6-[4-(3-pyridyl)butanoyl]-3,4-dihydrocarbostyril.

EXAMPLE 4

Preparation of 6-[1-hydroxy-2-(imidazol-1-yl)ethyl]-3,4-dihydrocarbostyril and related compounds of Formula IC and IG (a) A solution of 3.0 g of 6-(imidazol-1-ylacetyl)-3,4-dihydrocarbostyril (the preparation of which is given in Example 3) in 120 ml of methanol was reacted with 1.2 g of sodium borohydride in the same manner as shown in Preparation 2, and the product similarly isolated to give 6-[1-hydroxy-2-(imidazol-1-yl)ethyl]-3,4-dihydrocarbostyril, m.p. 182°–184°

(b) Following the procedure shown in paragraph (a) above, but starting with the appropriate compounds of Formula IB or IF, the following compounds of Formula IC and IG were prepared:
6-[hydroxy(3-pyridyl)methyl]-3,4-dihydrocarbostyril, m.p. 178°–180° C.; and
6-[1-hydroxy-2-(3-pyridyl)ethyl]-3,4-dihydrocarbostyril, m.p. 183°–185° C.

(c) Similarly, the following compounds of Formula IG are prepared:
6-[1-hydroxy-3-(3-pyridyl)propyl]-3,4-dihydrocarbostyril, and
6-[1-hydroxy-4-(3-pyridyl)butyl]-3,4-dihydrocarbostyril.

EXAMPLE 5

Preparation of 6-[1-hydroxy-1-phenyl-2-(imidazol-1-yl)ethyl]-3,4-dihydrocarbostyril and related compounds of Formula IG (a) A solution of 3 ml of 3M phenylmagnesium bromide in ether was added to a suspension of 1.0 g of 6-(imidazol-1-yl acetyl)-3,4-dihydrocarbostyril in 25 ml of tetrahydrofuran at 0° C., the mixture stirred for 30 minutes at 0° C., then at 25° C. for 18 hours. The reaction was quenched with 10 ml of water and extracted with 10% methanol in methylene chloride. The organic extract was washed with water, dried over anhydrous sodium sulfate and concentrated under reduced pressure to yield a gum which was chromatographed on silica gel, eluting with 5% methanol in methylene chloride, to give 6-[1-hydroxy-1-phenyl-2-(imidazol-1-yl)ethyl]-3,4-dihydrocarbostyril as a foam.

1H NMR (CDCl$_3$) δ 2.56 (d, 1H, J=8.1 Hz), 2.58 (d, 1H, J=8.1 Hz), 2.78 (s, 1H), 2.88 (t, 2H, J=8.1 Hz), 4.65 (s, 2H), 6.57 (s, 1H), 6.74 (d, 1H, J=8.82 Hz), 6.77 (s, 1H), 7.14 (m, 2H), 7.25 (s, 1H), 7.30–7.40 (m, 5H), 8.62 (s, 1H).

(b) Following the procedure described in paragraph (a) above, but starting with the appropriate compounds of Formula 1E or 1F in place of 6-(imidazol-1-ylacetyl)-3,4-dihydrocarbostyril and the appropriate compound of formula $R^1MgY$ in place of phenylmagnesium bromide, the following compounds of Formula IG were prepared:
6-[1-hydroxy-1-n-pentyl-2-(imidazol-1-yl)ethyl]-3,4-dihydrocarbostyril.

1H NMR (CDCl$_3$) δ 0.83 (t, 3H, J=5.3 Hz), 1.07–1.42 (m, 6H), 1.77 (m, 2H), 2.5–3.7 (m, 4H), 3.83 (s, 1H), 4.1 (s, 2H), 6.67–8.0 (series of unresolved multiplets, 6H), 8.51 (s, 1H).

6-[1-hydroxy-1-methyl-2-(imidazol-1-yl)ethyl]-3,4-dihydrocarbostyril.

1H NMR (CDCl$_3$) δ 1.30 (s, 3H), 2.41 (m, 2H), 2.85 (t, 2H, J=7.5 Hz), 4.08 (m, 2H), 5.38 (broad singlet, 1H), 6.76 (m, 2H), 6.94 (s, 1H), 7.14 (s, 1H), 7.23 (s, 1H), 7.39 (s, 1H), 10.01 (s, 1H).

(c) Following the procedure described in paragraph (a) above, but starting with the appropriate compounds of Formula IB or IF and the appropriate compound of formula $R^1MgY$ in place of phenylmagnesium bromide, the following compounds of Formula IC or IG were prepared:
6-[1-hydroxy-1-(3-pyridyl)ethyl]-3,4-dihydrocarbostyril, m.p. 88°–92° C.;

6-[1-hydroxy-1-methyl-2-(3-pyridyl)ethyl]-3,4-dihydrocarbostyril, m.p. 189°–190° C.;

6-[1-hydroxy-1-n-pentyl-2-(3-pyridyl)ethyl]-3,4-dihydrocarbostyril, m.p. 77°–80° C.; and 6-[1-hydroxy-1-phenyl-2-(3-pyridyl)ethyl]-3,4-dihydrocarbostyril, m.p. 118°–120° C.

(d) In a similar manner, starting with compounds of Formula IB, and following the procedure described in paragraph (a) above, the following compounds of Formula IC are prepared:

6-[1-hydroxy-1-(3-pyridyl)propyl]-3,4-dihydrocarbostyril;

6-[1-hydroxy-1-(3-pyridyl)butyl]-3,4-dihydrocarbostyril;

6-[1-hydroxy-1-(3-pyridyl)isobutyl]-3,4-dihydrocarbostyril;

6-[1-hydroxy-1-(3-pyridyl)pentyl]-3,4-dihydrocarbostryil;

6-[1-hydroxy-1-(3-pyridyl)-2-methylbutyl]-3,4-dihydrocarbostyril;

6-[1-hydroxy-1-(3-pyridyl)heptyl]-3,4-dihydrocarbostryil;

6-[1-hydroxy-1-(3-pyridyl)-4-phenylbutyl]-3,4-dihydrocarbostyril;

6-[hydroxy(4-chlorophenyl)(3-pyridyl)methyl]-3,4-dihydrocarbostyril;

6-[hydroxy(4-methoxyphenyl)(3-pyridyl)methyl]-3,4-dihydrocarbostyril;

6-[hydroxy(2,4-dimethylphenyl)(3-pyridyl)methyl]-3,4-dihydrocarbostyril; and

6-[1-hydroxy-1-(3-pyridyl)-2-phenylethyl]-3,4-dihydrocarbostyril.

(e) In a similar manner, starting with compounds of Formula IF, and following the procedure described in paragraph (a) above, the following compounds of Formula IG where Het is 3-pyridyl are prepared:

6-[1-hydroxy-1-n-propyl-2-(3-pyridyl)ethyl]-3,4-dihydrocarbostyril;

6-[1-hydroxy-1-isopropyl-2-(3-pyridyl)ethyl]-3,4-dihydrocarbostyril;

6-[1-hydroxy-1-n-butyl-2-(3-pyridyl)ethyl]-3,4-dihydrocarbostyril;

6-[1-hydroxy-1-sec-butyl-2-(3-pyridyl)ethyl]-3,4-dihydrocarbostyril;

6-[1-hydroxy-1-n-hexyl-2-(3-pyridyl)ethyl]-3,4-dihydrocarbostyril;

6-[1-hydroxy-1-(3-phenylpropyl)-2-(3-pyridyl)-ethyl]-3,4-dihydrocarbostyril;

6-[1-hydroxy-1-(4-chlorophenyl)-2-(3-pyridyl)ethyl]-3,4-dihydrocarbostyril;

6-[1-hydroxy-1-(4-methoxyphenyl)-2-(3-pyridyl)ethyl]-3,4-dihydrocarbostyril;

6-[1-hydroxy-1-(2,4-dimethylphenyl)-2-(3-pyridyl)ethyl]-3,4-dihydrocarbostyril; and 6-[1-hydroxy-1-benzyl-2-(3-pyridyl)ethyl]-3,4-dihydrocarbostyril.

(f) In a similar manner, starting with compounds of Formula IE, and following the procedure described in paragraph (a) above, the following compounds of Formula IG, where Het is 1-imidazolyl, are prepared:

6-[1-hydroxy-1-n-propyl-2-(imidazol-1-yl)ethyl]-3,4-dihydrocarbostyril;

6-[1-hydroxy-1-isoprpyl-2-(imidazol-1-yl)ethyl]-3,4-dihydrocarbostyril;

6-[1-hydroxy-1-n-butyl-2-(imidazol-1-yl)ethyl]-3,4-dihydrocarbostyril;

6-[1-hydroxy-1-sec-butyl-2-(imidazol-1-yl)ethyl]-3,4-dihydrocarbostyril;

6-[1-hydroxy-1-n-hexyl-2-(imidazol-1-yl)ethyl]-3,4-dihydrocarbostyril;

6-[1-hydroxy-1-(3-phenylpropyl)-2-(imidazol-1-yl)ethyl]-3,4-dihydrocarbostyril;

6-[1-hydroxy-1-(4-chlorophenyl)-2-imidazol-1-yl)ethyl]-3,4-dihydrocarbostyril;

6-[1-hydroxy-1-(4-methoxyphenyl)-2-(imidazol-1-yl)ethyl]-3,4-dihydrocarbostyril;

6-[1-hydroxy-1-(2,4-dimethylphenyl)-2-(imidazol-1-yl)ethyl]-3,4-dihydrocarbostyril; and 6-[1-hydroxy-1-benzyl-2-(imidazol-1-yl)ethyl]-3,4-dihydrocarbostyril.

EXAMPLE 6

Preparation of 6-[phenyl(3-pyridyl)methyl]-3,4-dihydrocarbostyril and related compounds of Formula ID (a) To a solution of 240 mg of 6-[1-hydroxy-1-phenyl(3-pyridyl)methyl]-3,4-dihydrocarbostyril in 5 ml of trifluoroacetic acid at 0° C. was added 280 mg of sodium borohydride. When hydrogen evolution ceased the mixture was stirred at 25° C. for 30 minutes, then the solvent was removed under reduced pressure. The residue was added to aqueous potassium carbonate solution and extracted with ethyl acetate. The organic layer was dried over anhydrous magnesium sulfate, the solvent removed under reduced pressure and the residue chromatographed on silica gel, eluting with 3% methanol in methylene chloride to give 6-[phenyl(3-pyridyl)methyl]-3,4-dihydrocarbostyril, m.p. 95°–96° C.

(b) Following the procedure described in paragraph (a) above, but starting with the appropriate compounds of Formula IC, the following compound of Formula ID was prepared:

6-[1-(3-pyridyl)ethyl]-3,4-dihydrocarbostyril,

1H NMR (CDCl$_3$) δ 1.63 (d, 2H, J=6.0 Hz), 2.50–3.00 (m, 4H), 5.50 (d, 1H, J=6.0 Hz), 6.67–7.67 (series of unresolved multiplets, 5H), 8.50 (m, 2H), 8.95 (s, 1H).

(c) In a similar manner, the following the procedure described in paragraph (a) above, the following compounds of Formula ID are prepared:

6-[(3-pyridyl)methyl]-3,4-dihydrocarbostyril;

6-[1-(3-pyridyl)hexyl]-3,4-dihydrocarbostyril;

6-[1-(3-pyridyl)propyl]-3,4-dihydrocarbostyril;

6-[1-(3-pyridyl)isobutyl]-3,4-dihydrocarbostyril;

6-[1-(3-pyridyl)pentyl]-3,4-dihydrocarbostyril;

6-[1-(3-pyridyl)-2-methylbutyl]-3,4-dihydrocarbostyril;

6-[-(3-pyridyl)heptyl]-3,4-dihydrocarbostyril;

6-[1-(3-pyridyl)-4-phenylbutyl]-3,4-dihydrocarbostyril;

6-[(4-chlorophenyl)-(3-pyridyl)methyl]-3,4-dihydrocarbostyril;

6-[(4-methoxyphenyl)-(3-pyridyl)methyl]-3,4-dihydrocarbostyril;

6-[(2,4-dimethylphenyl)-(3-pyridyl)methyl]-3,4-dihydrocarbostyril; and

6-[2-phenyl-1-(3-pyridyl)ethyl]-3,4-dihydrocarbostyril.

EXAMPLE 7A

Preparation of 6-[1-phenyl-2-(imidazol-1-yl)ethenyl]-3,4-dihydrocarbostyril and related compounds of Formula IH (a) A solution of 600 mg of 6-[1-hydroxy-1-phenyl-2-(imidazol-1-yl)ethyl]-3,4-dihydrocarbostyril in 20 ml of anhydrous formic acid was refluxed for 24 hours. The solvent was removed under reduced pressure and the residue partitioned between 5% methanol in methylene chloride and aqueous potassium carbonate. The organic solution was dried over anhydrous sodium sulfate and the solvent removed under reduced pressure. The residue was chromatographed on silica gel, eluting with 5% methanol in methylene chloride, affording 6-[1-phenyl-2-(imidazol-1-yl)ethenyl]-3,4-dihydrocarbostyril as a mixture of (E) and (Z) isomers.

1H NMR of major isomer (CDCl$_3$) δ 2.64 (d, 1H, J=8.0 Hz), 2.65 (d, 1H, J=8.0 Hz), 2.94 (t, 2H, J=8.0 Hz), 6.60 (t, 1H, J=1.33 Hz), 6.77 (d, 1H, J=8.1 Hz), 6.90 (t, 1H, J=1.1 Hz), 6.94–7.40 (series of unresolved multiplets, 9H), 8.50 (s, 1H).

(b) Following the procedure described in paragraph (a) of this Example, but starting with the appropriate compounds of Formula IG in place of 6-[1-hydroxy-1-phenyl-2-(imidazol-1-yl)ethyl]-3,4-dihydrocarbostyril, the following compounds of Formula IH were prepared as a mixture of (E) and (Z) isomers.

6-[2-(imidazol-1-yl)ethenyl]-3,4-dihydrocarbostyril, m.p. 199°–201° C.

6-[1-n-pentyl-2-(imidazol-1-yl)ethenyl]-3,4-dihydrocarbostyril,

1H NMR (CDCl$_3$) δ 0.83 (t, 3H, J=6.91 Hz), 1.25 (m, 4H), 1.37 (m, 2H), 2.52 (t, 2H, J=7.0 Hz), 2.69 (t, 2H, J=8.0 Hz), 3.02 (t, 2H, J=8.0 Hz), 6.77 (s, 1H), 6.91 (d, 1H, J=8.8 Hz), 7.00 (s, 1H), 7.16 (s, 1H), 7.23 (m, 2H), 7.58 (s, 1H), 9.61 (s, 1H);

6-[2-(3-pyridyl)ethenyl]-3,4-dihydrocarbostyril, m.p. 215°–217° C.;

6-[1-methyl-2-(imidazol-1-yl)ethenyl]-3,4-dihydrocarbostyril, m.p. 183°–185° C.;

6-[1-methyl-2-(3-pyridyl)ethenyl]-3,4-dihydrocarbostyril, m.p. 163°–165° C.;

6-[1-phenyl-2-(3-pyridyl)ethenyl]-3,4-dihydrocarbostyril, m.p. 202°–203° C.; and 6-[1-n-pentyl-2-(3-pyridyl)ethenyl]-3,4-dihydrocarbostyril, m.p. 189°–191° C.

(c) In a similar manner, following the procedure described in paragraph (a) above, the following compounds of Formula IH, where Het is 1-imidazolyl, are prepared:

6-[1-ethyl-2-(imidazol-1-yl)ethenyl]-3,4-dihydrocarbostyril;

6-[1-n-propyl-2-(imidazol-1-yl)ethenyl]-3,4-dihydrocarbostyril;

6-[1-isopropyl-2-(imidazol-1-yl)ethenyl]-3,4-dihydrocarbostyril;

6-[1-n-butyl-2-(imidazol-1-yl)ethenyl]-3,4-dihydrocarbostyril;

6-[1-sec-butyl-2-(imidazol-1-yl)ethenyl]-3,4-dihydrocarbostyril;

6-[1-n-hexyl-2-(imidazol-1-yl)ethenyl]-3,4-dihydrocarbostyril;

6-[1-(3-phenylpropyl)-2-(imidazol-1-yl)ethenyl]-3,4-dihydrocarbostyril;

6-[1-(4-chlorophenyl)-2-(imidazol-1-yl)ethenyl]-3,4-dihydrocarbostyril;

6-[1-(4-methoxyphenyl)-2-(imidazol-1-yl)ethenyl]-3,4-dihydrocarbostyril;

6-[1-(2,4-dimethylphenyl)-2-(imidazol-1-yl)ethenyl]-3,4-dihydrocarbostyril; and

6-[1-benzyl-2-(imidazol-1-yl)ethenyl]-3,4-dihydrocarbostyril.

(d) In a similar manner, following the procedure described in paragraph (a) above, the following compounds of Formula IH, where Het is 3-pyridyl, are prepared:

6-[1-ethyl-2-(3-pyridyl)ethenyl]3,4-dihydrocarbostyril;

6-[1-n-propyl-2-(3-pyridyl)ethenyl]-3,4-dihydrocarbostyril;

6-[1-isopropyl-2-(3-pyridyl)ethenyl]-3,4-dihydrocarbostyril;

6-[1-n-butyl-2-(3-pyridyl)ethenyl]-3,4-dihydrocarbostyril;

6-[1-sec-butyl-2-(3-pyridyl)ethenyl]-3,4-dihydrocarbostyril;

6-[1-n-hexyl-2-(3-pyridyl)ethenyl]-3,4-dihydrocarbostyril;

6-[1-(3-phenypropyl)-2-(3-pyridyl)ethenyl]-3,4-dihydrocarbostyril;

6-[1-(4-chlorophenyl)-2-(3-pyridyl)ethenyl]-3,4-dihydrocarbostyril;

6-[1-(4-methoxyphenyl)-2-(3-pyridyl)ethenyl]-3,4-dihydrocarbostyril;

6-[1-(2,4-dimethylphenyl)-2-(3-pyridyl)ethenyl]-3,4-dihydrocarbostyril; and

6-[1-benzyl-2-(3-pyridyl)ethenyl]-3,4-dihydrocarbostyril.

EXAMPLE 7B

Preparation of 6-[1-(imidazol-1-yl)prop-2-en-2-yl]-3,4-dihydrocarbostyril and related compounds of Formula IL (a) Following the procedure described in Example 7A above, starting with 6-[1-hydroxy-1-methyl-2-(imidazol-1-yl)ethyl]-3,4-dihydrocarbostyril in place of 6-[1-hydroxy-1-phenyl-2-(imidazol-1-yl)ethyl]-3,4-dihydrocarbostyril and separating the appropriate product by chromatography, the following compound of Formula IL was prepared:

6-[1-(imidazol-1-yl)prop-2-en-2-yl]-3,4-dihydrocarbostyril, m.p. 147°–149° C.

(b) Similarly, following the procedure described in paragraph (a) above, the following compounds of Formula IL, where Het is 1-imidazolyl, are prepared:

6-[1-(imidazol-1-yl)-but-2-en-2-yl]-3,4-dihydrocarbostyril;

6-[1-(imidazol-1-yl)-pent-2-en-2-yl]-3,4-dihydrocarbostyril;

6-[1-(imidazol-1-yl)-4-methylpent-2-en-2-yl]-3,4-dihydrocarbostyril;

6-[1-(imidazol-1-yl)-oct-2-en-2-yl]-3,4-dihydrocarbostyril;

6-[1-(imidazol-1-yl)-3-phenylprop-2-en-2-yl]-3,4-dihydrocarbostyril;

6-[1-(imidazol-1-yl)-3-(2-chlorophenyl)prop-2-en-2-yl]-3,4-dihydrocarbostyril;

6-[1-(imidazol-1-yl)-3-(4-methoxyphenyl)prop-2-en-2-yl]-3,4-dihydrocarbostyril.

(c) Similarly, following the procedure described in paragraph (a) above, the following compounds of Formula IL, where Het is 3-pyridyl, are prepared:

6-[1-(3-pyridyl)prop-2-en-2-yl]-3,4-dihydrocarbostyril;

6-[1-(3-pyridyl)-but-2-en-2-yl]-3,4-dihydrocarbostyril;

6-[1-(3-pyridyl)-pent-2-en-2-yl]-3,4-dihydrocarbostyril;

6-[1-(3-pyridyl)-4-methylpent-2-en-2-yl]-3,4-dihydrocarbostyril;

6-[1-(3-pyridyl)-oct-2-en-2-yl]-3,4-dihydrocarbostyril;

6-[1-(3-pyridyl)-3-phenylprop-2-en-2-yl]-3,4-dihydrocarbostyril;

6-[1-(3-pyridyl)-3-(2-chlorophenyl)prop-2-en-2-yl]-3,4-dihydrocarbostyril;

6-[1-(3-pyridyl)-3-(4-methoxyphenyl)prop-2-en-2-yl]-3,4-dihydrocarbostyril.

EXAMPLE 8

Preparation of
6-[1-phenyl-2-(imidazol-1-yl)ethyl]-3,4-dihydrocarbostyril and related compounds of Formula IK (a) A solution of 390 mg of a mixture of (E) and (Z) isomers of 6-[1-phenyl-2-(imidazol-1-yl)ethenyl]-3,4-dihydrocarbostyril in 10 ml of ethanol was stirred under hydrogen in the presence of 200 mg of a 10% palladium on charcoal catalyst until the theoretical amount of hydrogen had been absorbed. The catalyst was filtered off, the solvent removed from the filtrate under reduced pressure and the residue chromatographed on silica gel eluting with 5% methanol in methylene chloride, yielding 6-[1-phenyl-2-(imidazol-1-yl)ethyl]3,4-dihydrocarbostyril, having a melting point of 87°–94° C.

(b) Following the procedure described in paragraph (a) above, but starting with the appropriate compound of Formula IH, the following compounds of Formula IK were prepared:

6-[2-(imidazol-1-yl)ethyl]-3,4-dihydrocarbostyril, m.p. 137°–139° C.;
6-[1-methyl-2-(imidazol-1-yl)ethyl]-3,4-dihydrocarbostyril, m.p. 140°–142° C.; and
6-[1-n-pentyl-2-(imidazol-1-yl)ethyl]-3,4-dihydrocarbostyril, m.p. 192°–198° C.

(c) In a similar manner, the following compounds of Formula IK, where Het is 1-imidazolyl, are prepared:
6[1-ethyl-2-(imidazol-1-yl)ethyl]-3,4-dihydrocarbostyril;
6-[1-isopropyl-2-(imidazol-1-yl)ethyl]-3,4-dihydrocarbostyril;
6-[1-n-butyl-2-(imidazol-1-yl)ethyl]-3,4-dihydrocarbostyril;
6-[1-sec-butyl-2-(imidazol-1-yl)ethyl]-3,4-dihydrocarbostyril;
6-[1-n-hexyl-2-(imidazol-1-yl)ethyl]-3,4-dihydrocarbostyril;
6-[1-(3-phenylpropyl)-2-(imidazol-1-yl)ethyl]-3,4-dihydrocarbostyril;
6-[1-(4-chlorophenyl)-2-(imidazol-1-yl)ethyl]-3,4-dihydrocarbostyril;
6-[1-(4-methoxyphenyl)-2-(imidazol-1-yl)ethyl]-3,4-dihydrocarbostyril;
6-[1-(2,4-dimethylphenyl)-2-(imidazol-1-yl)-ethyl]-3,4-dihydrocarbostyril; and
6-[1-benzyl-2-(imidazol-1-yl)ethyl]-3,4-dihydrocarbostyril.

(d) In a similar manner, following the procedure described in paragraph (a) above, the following compounds of Formula IK, where Het is 3-pyridyl, are prepared:
b 6-[1-ethyl-2-(3-pyridyl)ethyl]-3,4-dihydrocarbostyril;
6-[1-isopropyl-2-(3-pyridyl)ethyl]-3,4-dihydrocarbostyril;
6-[1-n-butyl-2-(3-pyridyl)ethyl]-3,4-dihydrocarbostyril;
6-[1-sec-butyl-2-(3-pyridyl)ethyl]-3,4-dihydrocarbostyril;
6-[1-n-hexyl-2-(3-pyridyl)ethyl]-3,4-dihydrocarbostyril;
6-[1-(3-phenylpropyl)-2-(3-pyridyl)ethyl]-3,4-dihydrocarbostyril;
6-[1-(4-chlorophenyl)-2-(3-pyridyl)ethyl]-3,4-dihydrocarbostyril;
6-[1-(4-methoxyphenyl)-2-(3-pyridyl)ethyl]-3,4-dihydrocarbostyril;
6-[1-(2,4-dimethylphenyl)-2-(3-pyridyl)-ethyl]-3,4-dihydrocarbostyril; and
6-[1-benzyl-2-(3-pyridyl)ethyl]-3,4-dihydrocarbostyril.

EXAMPLE 9

Preparation of
6-[3-(imidazol-1-yl)prop-1-yn-1-yl]-3,4-dihydrocarbostyril, the compound of Formula IM (a) A mixture of 11.6 mg of cuprous iodide, 86 mg of bis (triphenylphosphine) palladium (II) dichloride, 1.5 g of 6-bromo-3,4-dihydrocarbostyril and 774 mg of N-propargylimidazole was stirred in a mixture of 10 ml of pyridine and 2 ml of triethylamine at 100° C. for 48 hours under nitrogen. The reaction was then treated with 10 ml of saturated aqueous potassium carbonate and extracted with a solution of 10% methanol in methylene chloride. The extract was dried over anhydrous sodium sulfate, the solvent removed under reduced pressure and the residue chromatographed on silica gel eluting with 4% methanol in methylene chloride, yielding 6-[3-(imidazol-1-yl)-prop-1-yn-1-yl]-3,4-dihydrocarbostyril, m.p. 164°–168° C.

(b) In a similar manner, replacing N-propargylimidazole with the appropriate compound of Formula E, and following the procedure described in paragraph (a) above, the following compounds of Formula IM are prepared:
6-[4-(imidazol-1-yl)but-1-yn-1-yl]-3,4-dihydrocarbostyril; and
6-[5-(imidazol-1-yl)pent-1-yn-1-yl]-3,4-dihydrocarbostyril.

EXAMPLE 10

Preparation of
6-[3-(imidazol-1-yl)prop-1-en-1-yl]-3,4-dihydrocarbostyril, the compound of Formula IN (a) A suspension of 75 mg of 5% palladium on barium sulfate catalyst in 8 ml of pyridine was stirred under hydrogen for 15 minutes. A solution of 502 mg of 6-[3-(imidazol-1-yl)prop-1-yn-1-yl]-3,4-dihydrocarbostyril in 3 ml of pyridine was added and the mixture stirred under hydrogen until the theoretical volume of hydrogen had been absorbed. The reaction mixture was filtered and the solvent removed from the filtrate under reduced pressure to give a residue which was recrystallized from a mixture of methanol and ethyl acetate to give 6-[3-(imidazol-1-yl)prop-1-en-1-yl]-3,4-dihydrocarbostyril, m.p. 158°–160° C.

(b) In a similar manner, replacing 6-[3-(imidazol-1-yl)prop-1-yn-1-yl]-3,4-dihydrocarbostyril with other compounds of Formula IM, and following the procedure described in paragraph (a) above, the following compounds of Formula IN are prepared:
6-[4-(imidazol-1-yl)but-1-en-1-yl]-3,4-dihydrocarbostyril; and
6-[5-(imidazol-1-yl)pent-1-en-1-yl]-3,4-dihydrocarbostyril.

EXAMPLE 11

Preparation of
6-[3-(imidazol-1-yl)propyl]-3,4-dihydrocarbostyril, the compound of Formula IP (a) A solution of 502 mg of 6-[3-(imidazol-1-yl)prop-1-yn-1-yl]-3,4-dihydrocarbostyril was stirred under hydrogen in the presence of 200 mg of a 10% palladium on charcoal catalyst as shown in Example 8, and the product was isolated in a similar fashion, giving 6-[3-

(imidazol-1-yl)propyl]-3,4-dihydrocarbostyril, m.p. 139°–141° C.

(b) In a similar manner, replacing 6-[3-(imidazol-1-yl)prop-1-yn-1-yl]-3,4-dihydrocarbostyril with the appropriate compound of Formula IN, and following the procedure described in paragraph (a) above, the following compound of Formula IP is prepared:
6-[4-(imidazol-1-yl)butyl]-3,4-dihydrocarbostyril.

EXAMPLE 12

Preparation of 6-[2-(3-pyridyl)ethynyl]-3,4-dihydrocarbostyril, the compound of Formula IQ A mixture of 11.6 mg of cuprous iodide, 86 mg of bis (triphenylphosphine)palladium(II)dichloride, 1.0 g of 6-ethynyl-3,4-dihydrocarbostyril and 3-bromopyridine were reacted as shown in Example 9, and the product isolated in a similar fashion, giving 6-[2-(3-pyridyl)ethynyl]-3,4-dihydrocarbostyril, m.p. 195°–197° C.

EXAMPLE 13

Preparation of 6-(imidazol-1-yl)-3,4-dihydrocarbostyril, the compound of Formula IS A mixture of 1.0 g of 6-bromo-3,4-dihydrocarbostyril, 300 mg of imidazole, 40 mg of cuprous iodide and 600 mg of potassium carbonate in 4 ml of N,N-dimethylformamide was heated at 90° C. for 48 hours. The reaction mixture was poured into water and extracted with a mixture of 10% methanol in methylene chloride. The organic layer was dried over anhydrous sodium sulfate, the solvent removed under reduced pressure and the residue chromatographed on silica gel, eluting with 3% methanol in methylene chloride, giving 6-(imidazol-1-yl)-3,4-dihydrocarbostyril, m.p. 205°–208° C.

EXAMPLE 14

Preparation of 6-(3-pyridyl)-3,4-dihydrocarbostyril, the compound of Formula IR

To a solution of 1.0 g of 6-bromo-3,4-dihydrocarbostyril, 520 mg of 3-pyridyldiethylborane and 205 mg. of tetrakis(triphenylphosphine)palladium in 20 ml of tetrahydrofuran was added 600 mg of powdered potassium hydroxide and 114 mg of tetrabutylammonium bromide. The mixture was refluxed for 48 hours under an inert atmosphere and the solvent then removed under reduced pressure. The residue was extracted with a mixture of 10% of methanol in methylene chloride and the organic solution washed with water and dried over anhydrous sodium sulfate. The solvent was removed from the dried solution under reduced pressure, and the residue chromatographed on silica gel, eluting with 5% methanol in methylene chloride to give 6-(3-pyridyl)-3,4-dihydrocarbostyril, m.p. 180°–182° C.

EXAMPLE 15

Preparation of 6-[2-(imidazol-1-yl)ethenyl]carbostyril and related compounds of Formula IU (a) To a solution of 1.5 g of 6-[2-(imidazol-1-yl)ethenyl]-3,4-dihydrocarbostyril in 15 ml of N,N-dimethylformamide was added 7.0 g of freshly prepared nickel peroxide. The suspension was stirred under nitrogen for 72 hours at room temperature, then filtered and solvent removed from the filtrate under reduced pressure. The residue was chromatographed on silica gel, eluting with 5% methanol in methylene chloride, to give 6-[2-(imidazol-1-yl)ethenyl]carbostyril, m.p. 211°–213° C.

(b) Following the procedure described in paragraph (a) above, but starting with the appropriate compound of Formula IA, the following compound of Formula IU was prepared: 6-[phenyl(imidazol-1-yl)methyl]carbostyril, m.p. 226°–228° C.

(c) In a similar manner, starting with the appropriate compounds of Formula I, and following the procedure described in paragraph (a) above, the following compounds of Formula IU are prepared:
6-[1-(imidazol-1-yl)ethyl]carbostyril;
6-[1-(imidazol-1-yl)hexyl]carbostyril;
6-[1-(imidazol-1-yl)-2-phenylethyl]carbostyril;
6-[1-(imidazol-1-yl)-2-(4-methoxyphenyl)ethyl]-carbostyril;
6-(imidazol-1-ylacetyl)carbostyril;
6-(3-pyridylacetyl)carbostyril;
6-[(3-pyridyl)phenylmethyl]carbostyril;
6-[1-(3-pyridyl)propyl]carbostyril;
6-[1-(3-pyridyl)heptyl]carbostyril;
6-[1-(3-pyridyl)-2-phenylethyl]carbostyril;
6-[(3-pyridyl)(4-methoxylphenyl)methyl]-carbostyril;
6-[1-phenyl-2-(imidazol-1-yl)ethenyl]carbostyril;
6-[1-(4-methoxyphenyl)-2-(imidazol-1-yl)ethenyl]-carbostyril;
6-[1-ethyl-2-(imidazol-1-yl)ethenyl]carbostyril;
6-[1-hexyl-2-(imidazol-1-yl)ethenyl]carbostyril;
6-[1-(4-phenylmethyl)-2-(imidazol-1-yl)ethenyl]carbostyril;
6-[1-phenyl-2-(imidazol-1-yl)ethyl]carbostyril;
6-[1-(4-methoxyphenyl)-2-(imidazolyl-1-yl)ethyl]-carbostyril;
6-[1-ethyl-2-(imidazolyl-1-yl)ethyl]carbostyril;
6-[1-hexyl-2-(imidazolyl-1-yl)ethyl]carbostyril;
6-[1-(4-phenylmethyl)-2-(imidazolyl-1-yl)ethyl]carbostyril;
6-[3-(imidazol-1-yl)prop-1-yn-1-yl]carbostyril;
6-[3-(imidazol-1-yl)prop-1-en-1-yl]carbostyril;
6-[3-(imidazol-1-yl)propyl]carbostyril;
6-[2-(3-pyridyl)ethynyl]carbostyril;
6-(imidazol-1-yl)carbostyril;
6-(3-pyridyl)carbostyril;
6-[1-phenyl-2-(3-pyridyl)ethenyl]carbostyril;
6-[1-ethyl-2-(3-pyridyl)ethenyl]carbostyril;
6-[1-hexyl-2-(3-pyridyl)ethenyl]carbostyril;
6-[1-benzyl-2-(3-pyridyl)ethenyl]carbostyril;
6-[1-(4-methoxyphenyl)-2-(3-pyridyl)ethenyl]-carbostyril;
6-[1-phenyl-2-(3-pyridyl)ethyl]carbostyril;
6-[1-ethyl-2-(3-pyridyl)ethyl]carbostyril;
6-[1-hexyl-2-(3-pyridyl)ethyl]carbostyril;
6-[1-benzyl-2-(3-pyridyl)ethyl]carbostyril;
6-[1-(4-methoxyphenyl)-2-(3-pyridyl)ethyl]carbostyril;

EXAMPLE 16

Conversion of Free Base to Salt (a) A twofold stoichiometric excess of a 3% solution of hydrogen chloride in methanol is added to a solution of 1.0 g of 6-[3-(imidazol-1-yl)propyl]-3,4-dihydrocarbostyril in 50 ml of methanol at 25° C. Diethyl ester is then added to the stirred solution until precipitation is complete. The precipitate is filtered off, washed with ether and recrystallized from a mixture of methanol and ethyl acetate to give 6-[3-(imidazol-1-yl)propyl]-3,4-dihydrocarbostyril hydrochloride.

(b) Similarly, following the procedures described in part (a) above, any compound of Formula I is converted to an acid addition salt.

EXAMPLE 17

Conversion of Salt to Free Base (a) A suspension of 1.0 g of 6-[3-(imidazol-1-yl)propyl]-3,4-dihydrocarbostyril hydrochloride in 100 ml of methylene chloride is stirred with a twofold stoichiometric excess of dilute aqueous sodium hydroxide solution until the salt is completely dissolved. The organic layer is separated, washed with water, dried over magnesium sulfate and evaporated to yield 6-[3-(imidazol-1-yl)propyl]-3,4-dihydrocarbostyril as the free base.

(b) Similarly, following the procedures described in part (a) above, any acid addition salt of a compound of Formula I is converted to its free base.

EXAMPLE 18

Direct Interchange of Acid Addition Salts (a) 6-[3-(imidazol-1-yl)propyl]-3,4-dihydrocarbostyril acetate (1.0 g) is dissolved in 50 ml of methanol and a stoichiometric amount of a solution of hydrochloric acid in methanol is added. The solvent is removed under vacuum and the residue recrystallised from a mixture of methanol and ethyl acetate to yield 6-[3-(imidazol-1-yl)propyl]-3,4-dihydrocarbostyril hydrochloride.

(b) Similarly, following the procedures described in part (a) above, any acid addition salt of a compound of Formula I is converted to another acid addition salt by reaction with an acid of a lower pKa.

EXAMPLES 19-23

In examples 19 through 23 the active ingredient is 6-[3-(imidazol-1-yl)propyl]-3,4-dihydrocarbostyril. However, other compounds of Formula I and the pharmaceutically acceptable salts thereof may be substituted therein.

EXAMPLE 19

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 20

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 21

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 22

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 23

A solution preparation buffered to a pH of 7 is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water | q.s. to 100 ml |

EXAMPLE 24

Determination of Inhibition and Thromboxane Synthetase Activity Utilizing Human Platelet Aggregation Human platelet-rich plasma preparation:

Blood sample is collected into siliconized vacutainers containing sodium citrate (0.5 ml of 11.25% sodium citrate per 15 ml vacutainer) final concentration 0.38%. Platelet rich plasma (PRP) is obtained after centrifuging the blood for 15 minutes at 200 xg at room temperature. Blood and plasma contacts only non-wettable plastic or siliconized glass surfaces.

Procedure:

1. Aggregation is followed by the turbidimetric method of Born (*J. Physiol.* 162, 67p, 1962), using a Payton Dual Channel Aggregometer.

2. PRP-PAM control. 1.0 ml PRP is used. Pig aortic microsomes (PAM), prepared according to Neichi, et al. (Prostaglandins, 19(4), 577–86 (1980)), are incubated in PRP at 37° C. with stirring for 3 minutes, immediately followed by addition of inducer-ADP. The concentration of PAM is chosen to show little or not inhibition of platelet aggregation when compared with the aggregation of PRP alone.

3. PRP-PAM plus thromboxane synthetase inhibitor. Thromboxane synthetase inhibitor is added to 1.0 ml PRP incubated at 37° C. with stirring for two minutes. The PAM concentration is chosen according to step 2, and is added to PRP incubated at 37° C. with stirring for another 3 minutes. The inducer ADP is added immediately afterwards.

EXAMPLE 25

Determination of Inhibition of Cyclic-AMP Phosphodiesterase Activity Utilizing Human Platelet Phosphodiesterase preparations Human platelet: Blood is obtained from donors who have not taken aspirin or similar medications for at least 2 weeks and is collected by venipuncture into evacuated glass tubes [Vacutainer, Becton, Dickinson, Rutherford, NJ] containing EDTA (7.7 nM, final concentration). PRP is obtained by centrifuging the blood in polycarbonate tubes at 200×g for 15 min at 4° C. All subsequent steps are performed at 4° C. A platelet pellet is obtained by further centrifugation of the PRP at 1000×g for 15 minutes. The pellet is resuspended in a volume of Buffer A (0.137M NaCl, 12.3 nM Tris-HCl buffer, pH 7.4 at 37° C., 1.54 mM EDTA, and 20 mM glucose) equal to the original PRP volume. The suspension is centrifuged at 1100×g for 15 minutes and the pellet is resuspended in Buffer A. The pellet is centrifuged at 1100×g and the pellets are resuspended in 0.5 ml of 50 mM Tris-HCl buffer, pH 7.7 containing 1 mM $MgCl_2$. The hypotonically-lysed platelet suspension is centrifuged at 48,000×g for 15 minutes and the supernatant is saved. The pellets are frozen on dry-ice and briefly thawed at 22° C. The supernatant is combined with the pellet fraction and the resulting suspension is centrifuged at 48,000×g for 30 minutes. The pellet and supernatant fractions are used as the crude membrane-bound and soluble enzyme preparations.

Cyclic-AMP Phosphodiesterase Assay

The phosphodiesterase incubation medium for all studies contains 12 mM Tris-HCl buffer, pH 7.7, 0.5 mM $MgCl_2$, 0.137M NaCl, 20 mM glucose, and appropriate concentrations of [$^3$H]-cyclic-AMP (0.2 μCi) in a total volume of 1.0 ml. Following addition of the enzyme the contents are mixed and incubated for 10 minutes at 30° C. The reaction is terminated by adding 10 μl of 0.1M EDTA, pH 7.0, mixing, and immediately immersing the tubes in a boiling water bath for 90 sec. Labeled adenosine is isolated from alumina columns according to the method of Filburn and Karn. Assays are performed in triplicate.

What is claimed is:

1. A compound of the formula:

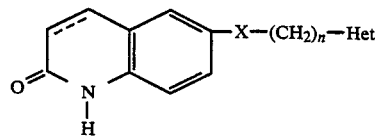

(I)

or a pharmaceutically acceptable acid addition salt or ester thereof, wherein:

X is chosen from the group consisting of:

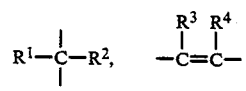

in which $R^1$ is H when $R^2$ is OH, or $R^1$ is phenyl or phenyl lower alkyl when $R^2$ is H or OH, wherein the phenyl radical is optionally monosubstituted with lower alkyl, lower alkoxy, hydroxy, trifluoromethyl or halogen, or $R^1$ and $R^2$ taken together represents oxo, alkylidene having 1–6 carbon atoms or optionally substituted benzylidene wherein the phenyl radical of the benzylidene group is optionally monosubstituted with lower alkyl, lower alkoxy, hydroxy, trifluoromethyl or halogen;

$R^3$ is H or alkyl having 1–6 carbon atoms, $R^4$ is H and $R^3$ and $R^4$ are either cis or trans to each other, or $R^3$ and $R^4$ taken together represent a covalent bond;

n is an integer from 0–3;

Het is 1-imidazolyl; and the dotted line represents an optional covalent bond.

2. The compound of claim 1, wherein X is

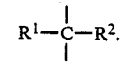

3. The compound of claim 2, wherein $R^1$ and $R^2$ taken together represent alkylidene having 1–3 carbon atoms and n is an integer from 1–3.

4. The compound of claim 2, wherein $R^1$ is phenyl, $R^2$ is H and n is 0.

5. The compound of claim 4, wherein $R^1$ is phenyl and the optional covalent bond represented by the dotted line is absent, namely 6-[phenyl(imidazol-1-yl)methyl]-3,4-dihydrocarbostyril.

6. The compound of claim 4, wherein $R^1$ is phenyl and the optional covalent bond represented by the dotted line is present, namely 6-[phenyl(imidazol-1-yl)methyl]carbostyril.

7. The compound of claim 1, wherein X is

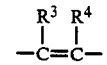

and n is 0 or 1.

8. The compound of claim 7, wherein $R^3$ and $R^4$ taken together represent a covalent bond.

9. The compound of claim 7, wherein $R^3$ is H or lower alkyl having 1–3 carbon atoms and $R^4$ is H.

10. The compound of claim 9, wherein $R^3$ is methyl, n is 0 and the optional covalent bond represented by the dotted line is absent, namely 6-[1-methyl-2-(imidazol-1-yl)ethenyl]-3,4-dihydrocarbostyril.

11. The compound of claim 9, wherein $R^3$ is H, n is 0 and the optional covalent bond represented by the dotted line is absent, namely 6-[2-(imidazol-1-yl)ethenyl]-3,4-dihydrocarbostyril.

12. The compound of claim 9, wherein $R^3$ is H, n is 0 and the optional covalent bond represented by the dotted line is present, namely 6-[2-(imidazol-1-yl)ethenyl]-carbostyril.

13. The compound of claim 9, wherein $R^3$ is H, n is 1 and the optional covalent represented by the dotted line is absent, namely 6-[3-(imidazol-1-yl)prop-1-en-1-yl]-3,4-dihydrocarbostyril.

14. A pharmaceutical composition for administration to a mammal having a disease characterized by elevated thromboxane levels or an imbalance of prostacyclin/thromboxane levels, which comprises a therapeutically effective amount of a compound of claim 1 in admixture with one or more pharmaceutically acceptable excipients.

* * * * *